(12) United States Patent
Nikitin et al.

(10) Patent No.: US 7,856,272 B2
(45) Date of Patent: Dec. 21, 2010

(54) IMPLANTABLE INTERFACE FOR A MEDICAL DEVICE SYSTEM

(75) Inventors: Alexei V. Nikitin, Lawrence, KS (US); Ivan Osorio, Leawood, KS (US); Mark G. Frei, Lawrence, KS (US); Naresh C. Bhavaraju, Lenexa, KS (US)

(73) Assignee: Flint Hills Scientific, L.L.C., Lawrence, KS (US)

( * ) Notice: Subject to any disclaimer, the term of this patent is extended or adjusted under 35 U.S.C. 154(b) by 419 days.

(21) Appl. No.: 11/414,736

(22) Filed: Apr. 28, 2006

(65) Prior Publication Data

US 2007/0272260 A1  Nov. 29, 2007

(51) Int. Cl.
*A61N 1/375* (2006.01)

(52) U.S. Cl. ...................................... 607/37

(58) Field of Classification Search .............. 607/37, 607/38, 45, 116
See application file for complete search history.

(56) References Cited

U.S. PATENT DOCUMENTS

| | | | |
|---|---|---|---|
| 5,336,253 A | 8/1994 | Gordon et al. | |
| 5,540,722 A | 7/1996 | Clare et al. | |
| 5,571,156 A | 11/1996 | Schmukler | |
| 5,632,957 A | 5/1997 | Heller et al. | |
| 5,674,267 A | 10/1997 | Mir et al. | |
| 5,718,719 A | 2/1998 | Clare et al. | |
| 5,776,173 A | 7/1998 | Madsen, Jr. et al. | |
| 5,782,891 A * | 7/1998 | Hassler et al. | 607/36 |
| 5,843,135 A | 12/1998 | Weijand et al. | |
| 6,038,480 A | 3/2000 | Hrdlicka et al. | |
| 6,055,453 A | 4/2000 | Hofmann et al. | |
| 6,068,650 A | 5/2000 | Hofmann et al. | |
| 6,122,296 A * | 9/2000 | Shih | 370/532 |
| 6,216,034 B1 | 4/2001 | Hofmann et al. | |
| 6,245,508 B1 | 6/2001 | Heller et al. | |
| 6,248,080 B1 | 6/2001 | Miesel et al. | |
| 6,391,024 B1 | 5/2002 | Sun et al. | |
| 6,418,348 B1 | 7/2002 | Witte | |
| 6,473,653 B1 | 10/2002 | Schallhorn et al. | |
| 6,480,572 B2 | 11/2002 | Harris et al. | |
| 6,560,486 B1 * | 5/2003 | Osorio et al. | 607/45 |
| 6,573,636 B1 | 6/2003 | Iino et al. | |
| 6,582,660 B1 | 6/2003 | Heller et al. | |
| 6,678,558 B1 | 1/2004 | Dimmer et al. | |
| 6,859,667 B2 | 2/2005 | Goode | |
| 7,346,391 B1 * | 3/2008 | Osorio et al. | 607/2 |

(Continued)

FOREIGN PATENT DOCUMENTS

EP  0269846  8/1988

(Continued)

*Primary Examiner*—Carl H Layno
*Assistant Examiner*—Gary A Porter, Jr.
(74) *Attorney, Agent, or Firm*—Banner & Witcoff, Ltd.

(57) ABSTRACT

An implantable interface system for a medical device system providing selective interconnectivity between conduits and therapy elements. The interface system contains connecting elements that each provide a robust connection between a selected conduit and a selected therapy element. The interface system enables the use of a surplus of therapy elements so that treatment to the same site (in the case of electrode migration or failure), or to different sites but within the spatial domain of the interface's elements may be delivered through the spare/excess therapy elements without the need for additional major surgical procedures.

9 Claims, 23 Drawing Sheets

U.S. PATENT DOCUMENTS

| | | |
|---|---|---|
| 2002/0126798 A1 | 9/2002 | Harris et al. |
| 2002/0193833 A1 | 12/2002 | Dimmer et al. |
| 2003/0088303 A1 | 5/2003 | Goode |
| 2003/0093130 A1 | 5/2003 | Stypulkowski |
| 2003/0149456 A1 | 8/2003 | Rottenberg et al. |
| 2003/0204232 A1 | 10/2003 | Sommer et al. |
| 2004/0034392 A1* | 2/2004 | Spadgenske ............... 607/37 |
| 2004/0068301 A1 | 4/2004 | Waltman et al. |
| 2004/0138711 A1 | 7/2004 | Osorio et al. |
| 2004/0152958 A1* | 8/2004 | Frei et al. ............... 600/300 |
| 2004/0158119 A1 | 8/2004 | Osorio et al. |
| 2004/0176817 A1* | 9/2004 | Wahlstrand et al. ......... 607/45 |
| 2005/0043768 A1 | 2/2005 | Goode |
| 2005/0165464 A1* | 7/2005 | Parker et al. .............. 607/115 |
| 2005/0245982 A1* | 11/2005 | Kast et al. ................. 607/36 |
| 2005/0259491 A1* | 11/2005 | Yarbrough et al. ......... 365/222 |
| 2006/0173522 A1* | 8/2006 | Osorio ..................... 607/116 |
| 2006/0282126 A1* | 12/2006 | Fischbach et al. ........... 607/37 |

FOREIGN PATENT DOCUMENTS

| | | |
|---|---|---|
| EP | 0737447 | 10/1996 |
| WO | 9422526 | 3/1994 |
| WO | 9531248 | 11/1995 |
| WO | 0056395 | 9/2000 |
| WO | 0078239 | 12/2000 |
| WO | 03041795 | 5/2003 |

* cited by examiner

Closed Position

Open Position

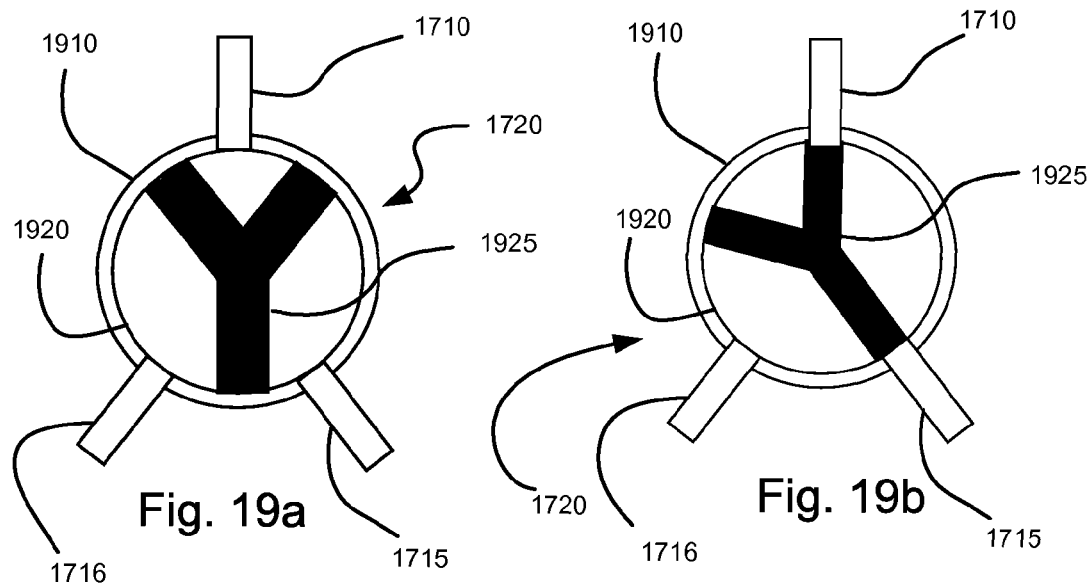
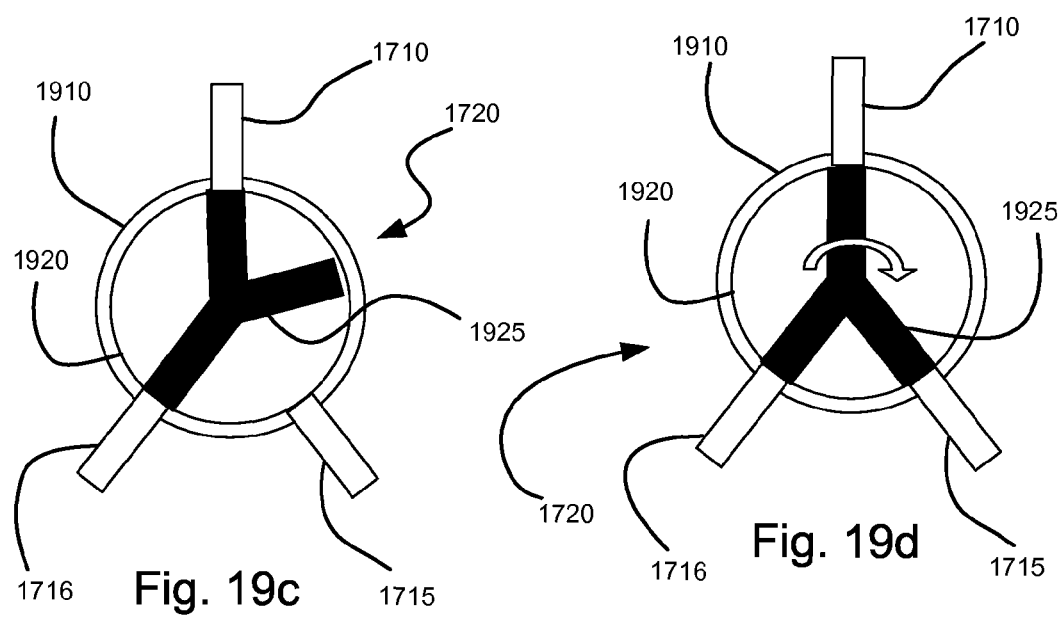

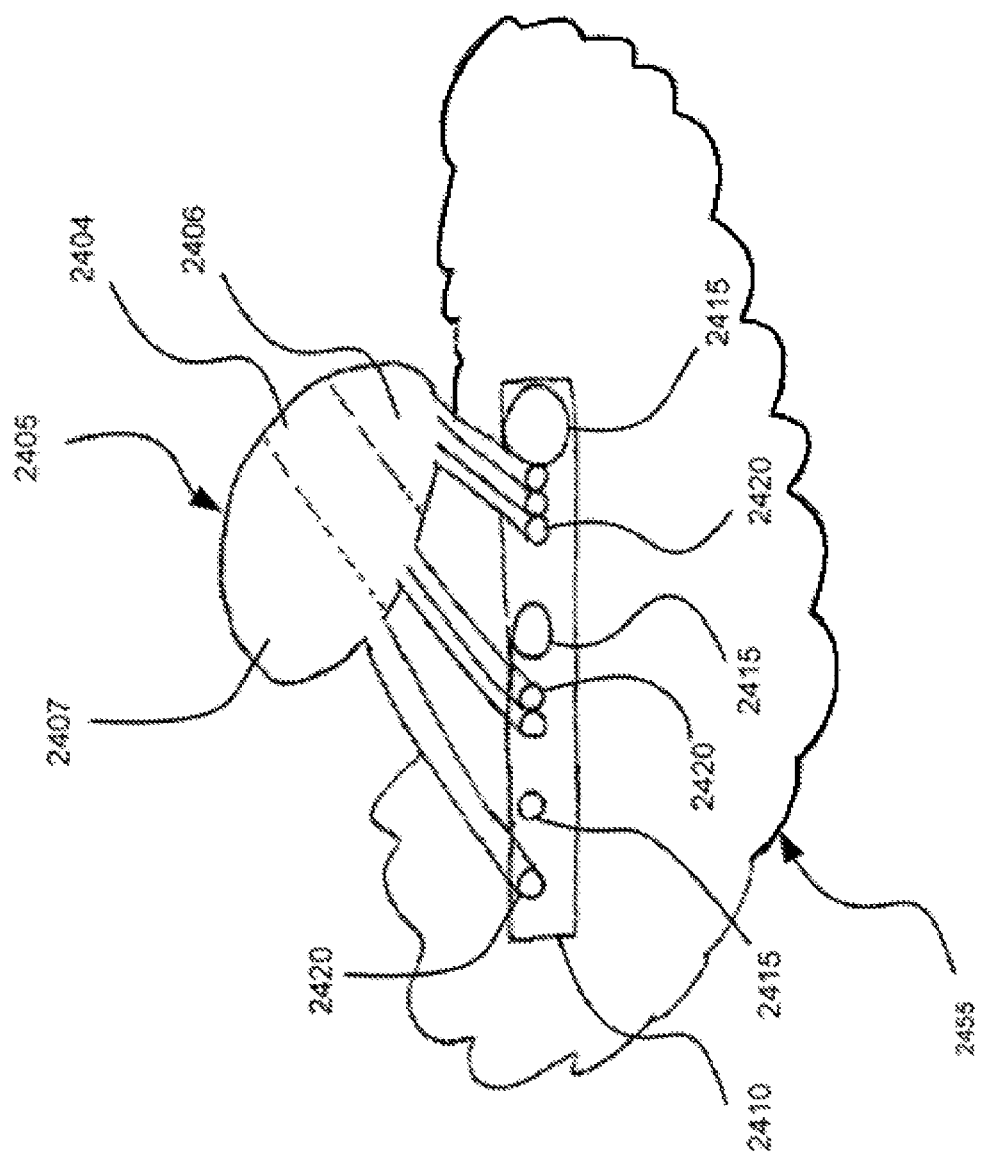

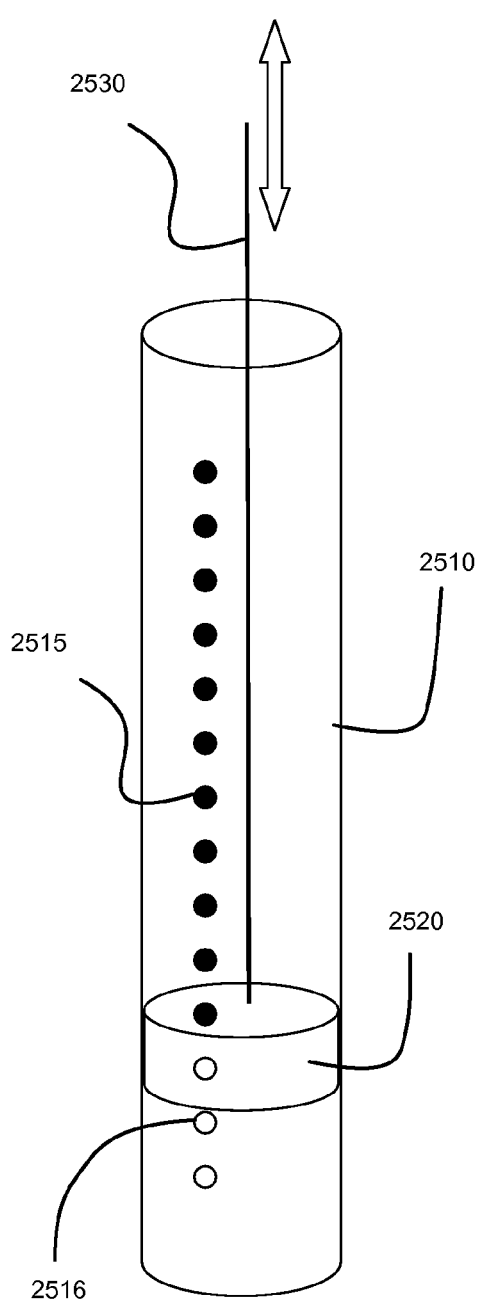
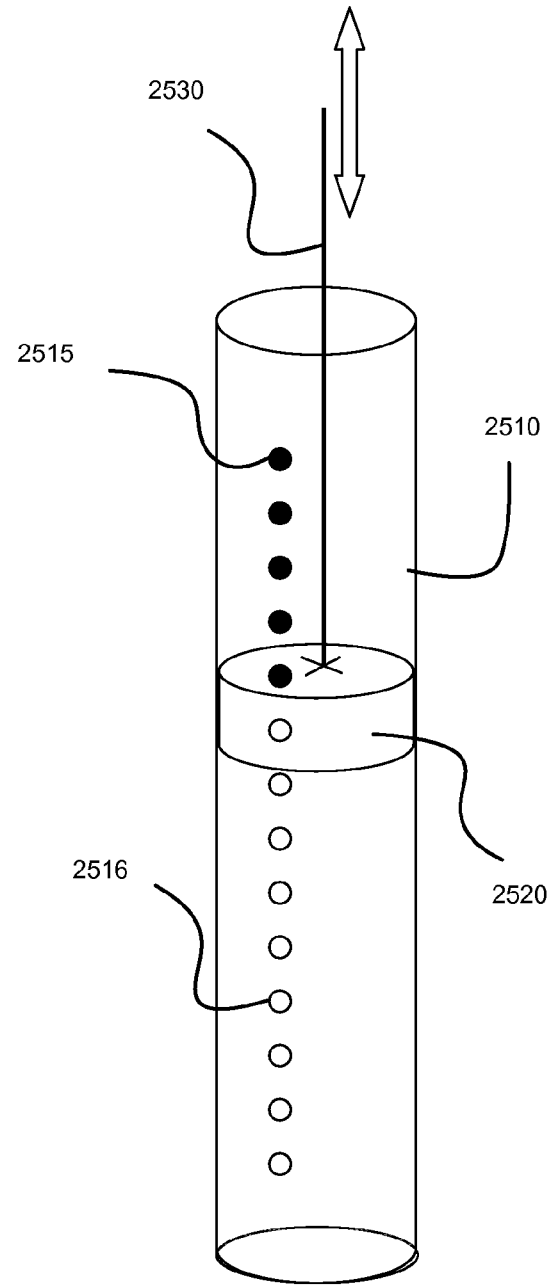
Fig. 25a
Fig. 25b

IMPLANTABLE INTERFACE FOR A MEDICAL DEVICE SYSTEM

FIELD OF THE INVENTION

The invention relates to the field of implantable systems for selecting therapy elements to monitor the status of and/or delivery therapy to tissue within a patient. More particularly, the invention provides convenient, non-invasive or minimally-invasive selection of a subset from a surplus of therapy elements previously implanted into tissue for connection with a (subset) of device conduits. The interface system may enable communication in a bi-directional manner (from device to tissue and from tissue to device) using the same therapy element(s) and/or conduits(s).

BACKGROUND

Electrical stimulation of the brain has been used to treat any number of neurological disorders including, for example, pain and movement disorders. Electrical leads having many electrodes are implanted in the brain such that one or more cathodal electrodes and one or more anodal electrodes are in optimal locations to produce benefits or to minimize undesirable side effects. An implantable pulse generator (IPG) generates signals to deliver electrical stimulation to the brain tissue via the electrodes. These electrodes or electrodes in other leads, may be also used to record electrical signals that, once adequately processed and analyzed using implantable or portable devices, may be used to monitor the state of the tissue or organ and to also deliver a therapy when this state is approaching abnormalcy. Additionally or alternatively, sets of inputs catheters carrying drugs may be selectively connected to sets of output catheters for drug delivery to surrounding tissue.

Depending on the disorder, sensing and or therapy systems may utilize a large number of electrodes or catheters to monitor and treat the disorder. Accordingly, the treating physician may configure the system with a spatial configuration of cathodes and anodes or of catheters that is best suited for any particular disorder or patient. If required, the treating physician may later optimize the electrode or catheter spatial configuration by selecting different electrodes or catheters from those originally chosen. Also, leads/electrodes or catheters may shift or migrate (in reference to the intended monitoring or therapy target) after being implanted, the chosen electrodes or catheters may "break," or the intended target site may change over time. To either improve the therapeutic benefits or to replace malfunctioning or off-target electrodes or catheters in prior-art implanted medical devices often requires a major surgical procedure.

Therefore, it is desirable to: a) implant more sensing and/or therapy elements than those actually used (i.e., those which sense electrical signals and/or through which currents or drugs are actually delivered to tissue) so that, by switching certain elements OFF and others ON, electrical currents or drugs continue to be delivered to the intended target or to a new one located within the spatial domain/reach of the sensing and/or therapy elements; and b) accomplish these tasks without further surgery.

Therefore, there exists a need in the art for implantable interfaces for electrical monitoring and/or stimulation and/or for drug delivery having a plurality/surplus of electrodes or catheters that may be selectively chosen and coupled to monitor tissue electrical signals and deliver electrical stimulation or drugs to desired neural tissue, without exceeding or violating size constraints for implantability and/or without requiring additional surgeries.

SUMMARY

The following represents a simplified summary of some embodiments of the invention in order to provide a basic understanding of various aspects of the invention. This summary is not an extensive overview of the invention. It is not intended to identify key or critical elements of the invention or to delineate the scope of the invention. Its sole purpose is to present some embodiments of the invention in simplified form as a prelude to the more detailed description that is presented below.

In accordance with aspects of the invention, an implantable interface system for a medical device system is disclosed. The interface system enables the flexible and efficient utilization of a surplus of sensing and/or therapeutic elements (i.e., therapy elements), allowing an optimal subset of these elements to be selected for use (and later modified if necessary) without major surgery that would otherwise be required to reposition, replace or activate more therapy elements. The interface system thus enables, for example, an increase in the available size of the electrical field or of the area to which drugs are delivered, while keeping the size of the hardware/device small so that it can be safely and ergonomically implanted. The interface system provides selective, re-programmable interconnectivity between a plurality/surplus of inputs and a plurality/surplus outputs that may be operated bi-directionally (inputs become outputs and vice-versa) depending on the application. These therapy elements may be implanted into or near an organ of a patient, for example, a brain. The interface system enables the use of a surplus of therapy elements so that treatment to the same site (in the case of electrode migration or failure), or to different sites but within the spatial domain of the interface's elements may be delivered through the spare/excess therapy elements without the need for additional major surgical procedures. For example, without further major surgery, the interface system may be used to select from a surplus of therapy elements to selectively determine which subset is used to provide input to a monitoring device. Alternatively, the interface system also enables selection of a subset of therapy elements (e.g., stimulation contacts or catheters) to be used as outputs to deliver therapy (e.g., stimulation or drugs, respectively).

In an embodiment, the interface system may include two plates. A first plate may be coupled to the conduits via one or more first plate contact points. The second plate may be coupled to the therapy element via one or more second plate contact points. One or more connecting elements may be positioned between the first and second plates, wherein each connecting element provides a robust electrical connection between a selected conduit and a selected therapy element. In an embodiment, the connecting element provides physical contact between the first plate contact point associated with the selected conduit and the second plate contact point associated with the selected therapy element. In an embodiment, a middle plate may be provided between the first and second plates to facilitate positioning of the connecting elements. In an embodiment, a spring mechanism may also be provided within the interface system to ensure adequate electrical connection provided by the connecting elements. The interface system may be encapsulated in a housing that may include a cover such as a membrane so as to ensure a fluid-tight seal.

In accordance with another aspect of the present invention, one or more valves may be provided to couple one or more inlet tubes with a plurality of delivery/outlet tubes. In an embodiment, an inlet tube may be adjustably connected to a plurality of delivery tubes. A series of valves may be coupled together in a module so that fluid from a reservoir may be selectively delivered to one or more delivery tubes so as to delivery fluid to the patient in a desired two dimensional or three dimensional pattern. The amount of fluid being delivered to each delivery tube may be adjustable. The system can also be used bi-directionally, for example, to sample fluids from a plurality of sites and store them in chambers.

BRIEF DESCRIPTION OF THE DRAWINGS

The present invention is illustrated by way of example and not limited in the accompanying figures in which like reference numerals indicate similar elements and in which:

FIGS. 19a-19d illustrate cross-sections of an embodiment of a valve in different configurations in accordance with one or more aspects of the present invention.

FIG. 24 illustrates a system configured to provide an adjustable fluid delivery in accordance with one or more aspects of the present invention.

FIGS. 25a-25c illustrate an embodiment of a delivery tube capable of delivering an adjustable flow rate to adjustable/different sites in accordance with one or more aspects of the present invention.

DETAILED DESCRIPTION

Aspects of the invention may be embodied in any implantable medical device system wherein a component of the system is to be implanted within a patient to monitor tissue electrical signals and/or provide therapy in the form of electrical stimulation or drug delivery. The implantable interface system discussed herein may have physical attributes (length/width/thickness, consistency and weight) that will allow implantation avoiding or minimizing the potential for causing injury to the brain or spinal cord or discomfort to the patient, while maximizing precision and degree of contact between the device elements and the therapy targets or sites. An embodiment of the invention may utilize various treatment therapies for treating nervous system disorders. Treatment therapies can include any number of possibilities alone or in combination including, for example, electrical stimulation, drug delivery and/or providing a warning of impending undesirable events to the patient or to caregivers.

Each of these treatment modalities may be operated using closed-loop feedback control or using open-loop therapy. Such closed-loop feedback control techniques receive one or more signals that carry information about a symptom or a condition of a nervous system disorder. Such signals can include, for example, electrical signals (such as EEG, ECoG and/or EKG), bio-chemical signals (such as change in quantity of neurotransmitters), temperature signals, pressure signals (such as blood pressure, intracranial pressure or cardiac pressure), respiration signals, heart rate signals, pH-level signals, and/or peripheral nerve signals (cuff electrodes on a peripheral nerve). Such signals may be recorded using one or more monitoring elements such as monitoring electrodes or sensors. For example, U.S. Pat. No. 6,227,203, assigned to Medtronic, Inc., provides examples of various types of monitoring elements that may be used to detect a symptom or a condition or a nervous system disorder and responsively generate a neurological signal.

Figure 1:
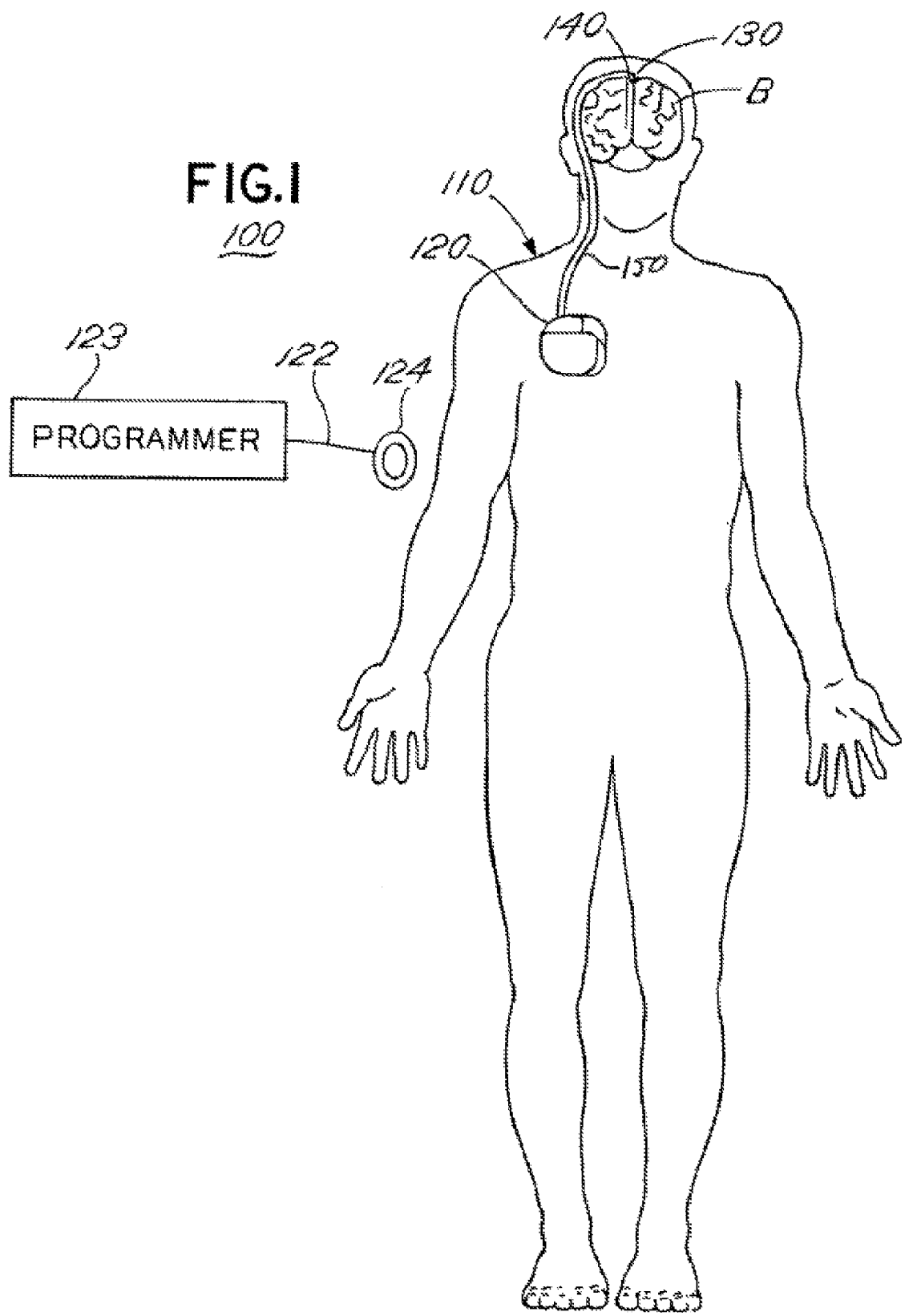
FIG. 1 schematically depicts an implantable medical device system providing electrical stimulation or some other form of therapy to the brain and/or sensing a characteristic of the brain.

In accordance with one set of embodiments, the implantable interface system is associated with a therapy delivery element or a monitoring element or a combination of both (dual function). FIG. 1 schematically represents these embodiments and depicts an implantable medical device system 100 that provides treatment therapy to the brain and/or monitors a characteristic of the brain B. The medical device system 100 generally includes a device 120 capable of being implanted in a patient 110 and coupled to one or more therapy delivery elements 130 and/or one or more monitoring elements 140 via one or more conduits 150 or in a wireless manner. The therapy delivery elements 130 deliver treatment therapy to a patient's nervous tissue (e.g., the brain). Likewise, the monitoring elements 140 monitor or sense one or more characteristics of nervous tissue (e.g., brain, spinal cord) or of other organ and can be the same device as the therapy delivery elements 130. Therapy delivery elements 130 or monitoring elements 140 may comprise one or more stimulation electrodes and may be implanted, by conventional stereotactic surgical techniques, into a structure of the brain such as the thalamus, the internal capsule, the globus pallidus, the subthalamic nucleus, or other neural structure. Alternatively or additionally, therapy delivery elements 130 or monitoring elements 140 may comprise one or more delivery tubes (e.g., catheters). Therapy elements 130 and/or 140 may be surgically implanted through a hole in a patient's skull and a remaining portion of the lead may be implanted between the patient's skull and scalp. Each therapy element may include one or more electrodes along its body.

As used herein, the term "therapy elements" refers generally to the structures of the medical device system providing therapy and/or monitoring a condition. For example, therapy elements include therapy delivery elements 130 and/or monitoring elements 140. As another example, discussed herein, therapy elements may include catheters (or tubes) for delivering fluid to the patient or receiving fluid from the patient.

The implantable device 120 may continuously or intermittently communicate with an external programmer 123 (e.g., patient or physician programmer) via telemetry using, for example, radio-frequency signals and having a coil 124 and a lead 122 coupling the programmer 123 with the coil 124. The external programmer 123 may be any general-purpose computing device (e.g., personal computer, hand-held device, etc.) having an operating system configured with custom external system application software.

In an embodiment where the medical device system 100 includes a brain stimulation system, the medical device system 100 delivers electrical stimulation to the brain through the therapy delivery elements 130. In the event that the medical device system 100 also utilizes closed-loop feedback control, the medical device system 100 monitors Brain Electrical Activity (BEA) or some other signal from the monitoring elements 140, conditions the brain signals for processing, determines the onset, presence, and/or intensity of any neurological event, configures the parameters for delivering electrical stimulation through the therapy delivery elements 130 if any should be provided.

Figure 2:
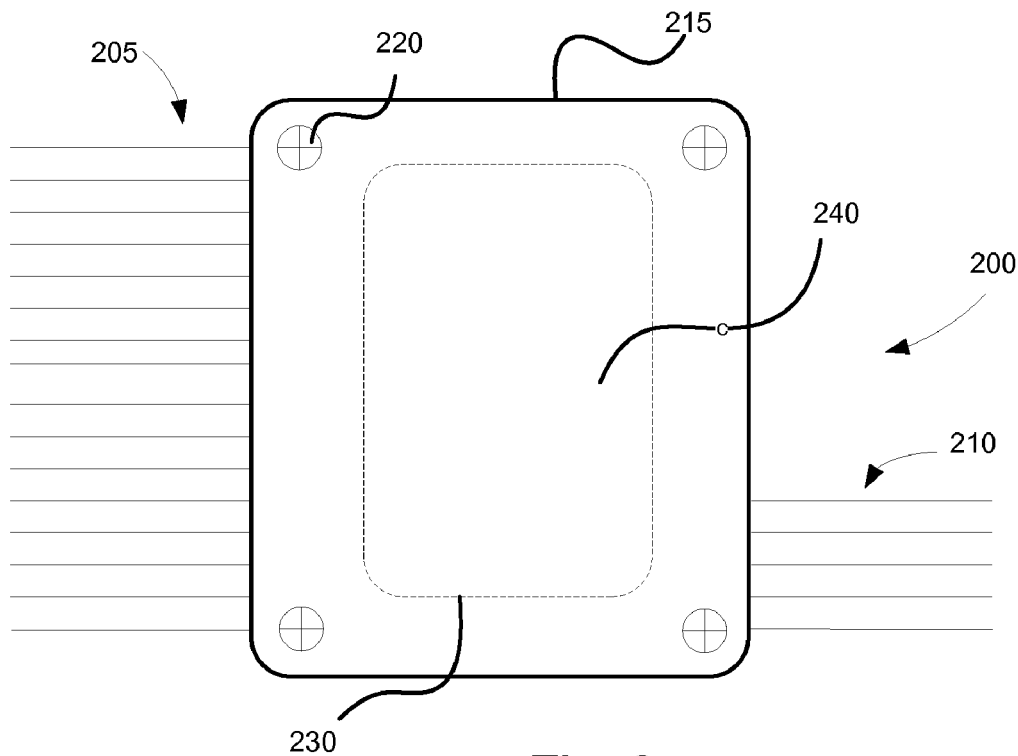
FIG. 2 depicts an implantable interface system in accordance with one or more aspects of the present invention.

The medical device system 100 also includes an implantable interface system interconnecting therapy elements 130 and/or 140 with the conduits 150. FIG. 2 depicts an embodiment of an interface system 200 for the implantable medical device system. The interface system 200 may be constructed of titanium or other suitable, bio-compatible material having necessary physical characteristics to mate with the patient's skull. In an embodiment, the interface system 200 comprises 16 sets of therapy elements 205 and 5 conduits 210. As will be discussed below, interface system 200 is contained within a sealed housing 215 so as to provide a fluid-tight seal between components within the interface system and the patient. The housing 215 may be fastened together with fasteners 220 and may include an opening covered by a membrane 240, impermeable to fluids (discussed below with respect to FIG. 8).

Figure 3:
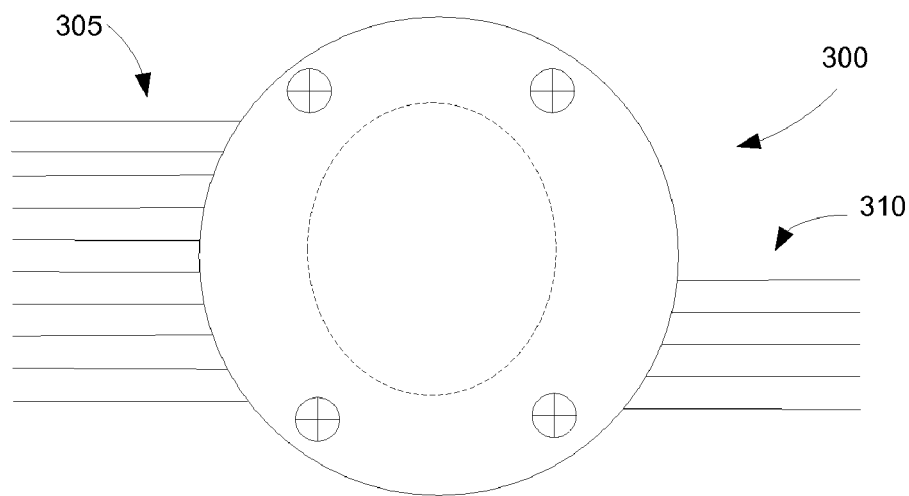
FIG. 3 shows one of many possible shapes of an implantable interface system and of its inputs and outputs in accordance with one or more aspects of the present invention.

FIG. 3 depicts an embodiment with a circular interface system 300, however, the interface system may take any number of geometric shapes depending on the particular application, location of implant, and/or design considerations. The interface system may include a plurality of conduits 310 delivering electrical stimulation energy from a signal generator, which through a plurality of therapy elements 305 deliver stimulation energy to desired regions of the body (and/or monitoring a condition). Optionally, the interface system may have a key to enable adjustment of the activated therapy elements (discussed further herein). As discussed, the interface system enables the use of a surplus of therapy elements to monitor/treat the same site (in the case of electrode migration), or to monitor/treat different sites within the spatial domain of the therapy elements (through the "spare" therapy elements), both of which is achieved without the need for additional surgical procedures and devices.

Also, as used herein, the term "conduit" refers generally to the structures of medical device system that interconnects the implantable device to the interface system. For example, conduits may be conduits 310 that provide/receive electrical signals between the implantable device and the interface system. As another example, discussed herein, conduits may include catheters (or tubes) for delivering or receiving fluid between the implantable device and the interface system.

Figure 4:
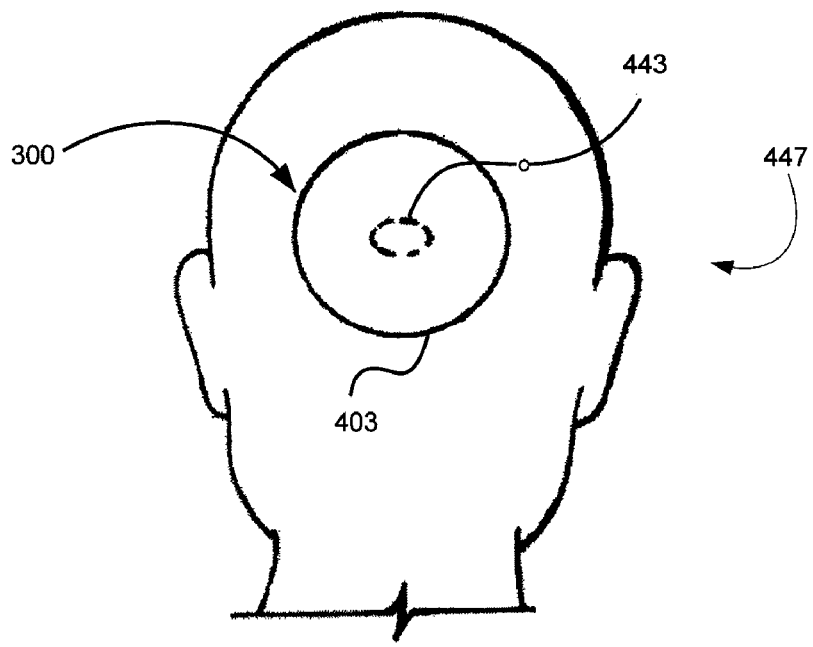
FIGS. 4 and 5 illustrate an embodiment of an implantable interface system implanted within a skull of a patient in accordance with one or more aspects of the present invention.
Figure 5:
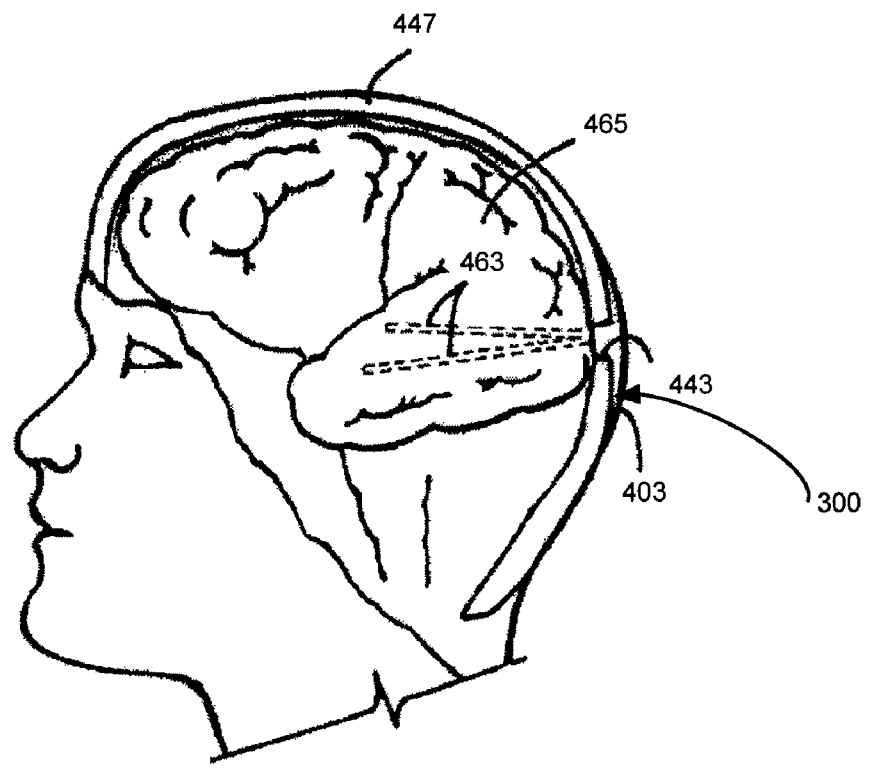

FIGS. 4 and 5 illustrate an embodiment where the interface system is configured to be positioned adjacent a skull of a patient. Depending on the application, the interface system may be placed over the skull, subdurally, or within a cavity formed in the skull. The interface system may be fixated to the skull through a variety of known techniques. For example, the interface system 403 may be configured to be partially (or completely) spaced in a cavity 443 formed in a patent's skull 447 (with appropriate modification to cavity 443). The interface system 403 may be attached to the patient's skull 447 and sealed to provide a fluid-tight seal between the interface system 403 and the patient's skull 447, dura mater, brain, and scalp. The interface system 403 may include therapy elements 463 (shown in dotted line) for providing therapy (either electrical stimulation or drug delivery or both) positioned within the patient's neurological tissue 465. The interface system 403 may contain other components to provide additional functionality, for example, such as a control mechanism, a microprocessor, a communication mechanism, and/or a power source (not shown) set forth in U.S. Pat. No. 6,560,486.

The interface system 403 may be configured so as to comport with the physical contours of the patient's skull. For example, in the embodiment where the interface system 403 is implanted within a cavity 443 within the patient's skull, the interface system 403 may have an inner wall surface that is substantially aligned with a surrounding inner surface of the patient's skull. Such alignment simulates the original physical surroundings of the patient's brain to avoid trauma thereto. If desired for a particular application, dura mater may be removed and the inner wall of the interface system may be placed in direct contact with the subject's cerebral spinal fluid/brain, for example, as described in U.S. patent application Ser. No. 11/339,108 filed on Jan. 25, 2006 and entitled "Anchoring of Medical Device Component Adjacent a Dura of the Brain or Spinal Cord."

Figure 6:
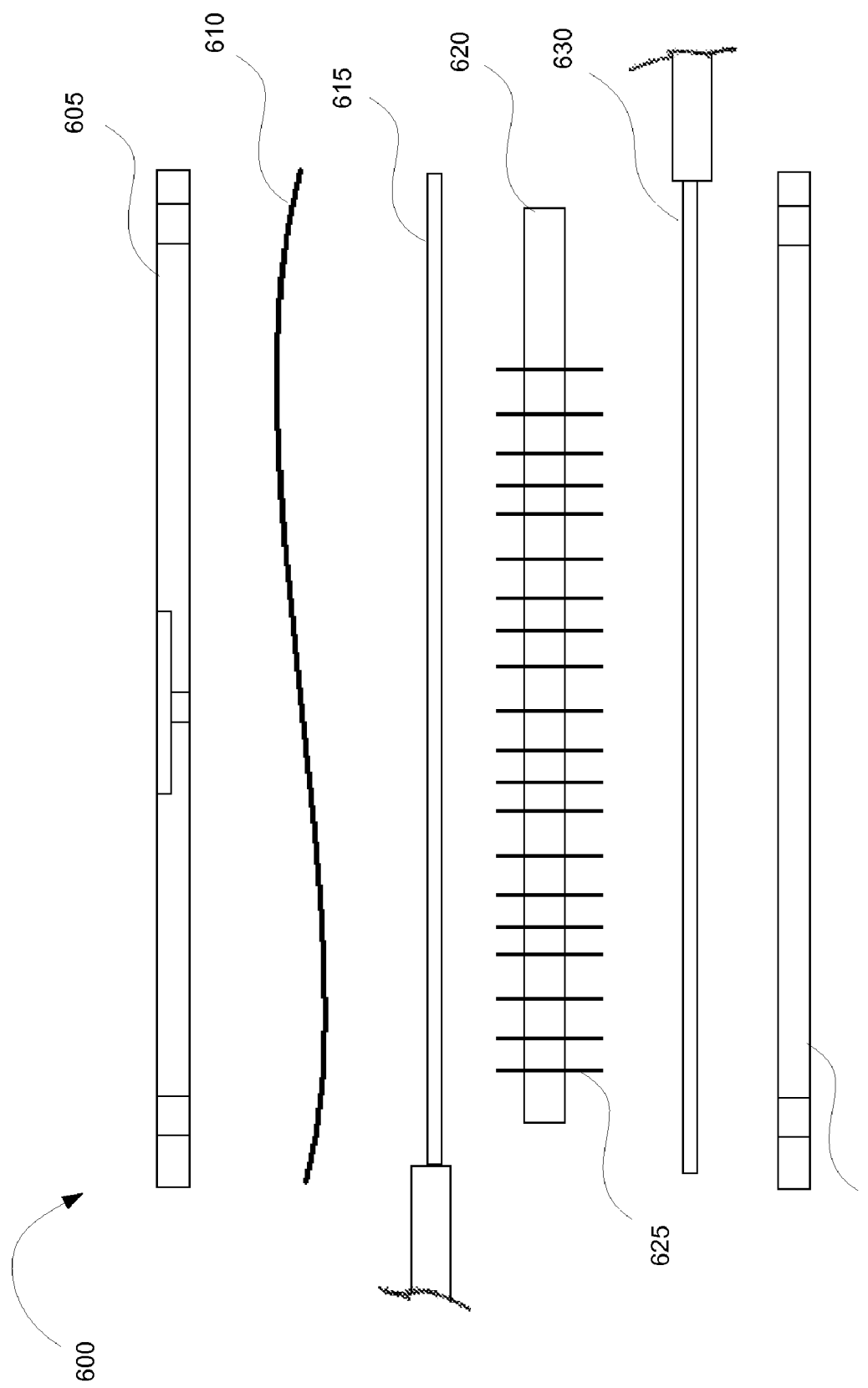
FIG. 6 is a partial exploded cross-sectional view of the various components of an implantable interface system in accordance with one or more aspects of the present invention.

FIG. 6 depicts an embodiment of specific components of an interface system 600. The interface system 600 provides an interface for the medical device system and generally comprises a top cover 605, an optional spring washer 610, a top plate 615, a middle plate 620, a bottom plate 630, a bottom cover 640, and connecting elements 625 each providing an electrical connection between a conduit and a therapy element. In the embodiment, each therapy element is associated with a contact point in the base plate 630. Each conduit, at one end, is coupled to a contact point in the top plate 615 and, at the opposite end, is coupled to a signal generator.

As can be appreciated, FIG. 6 depicts an embodiment of the specific components of an interface system 600. As depicted, the interface system 600 has a first plate that is coupled to one or more conduits via one or more first plate contact points. The second plate is coupled to one or more therapy elements via one or more second plate contact points. One or more connecting elements are provided wherein each connecting element provides a robust electrical connection between a selected conduit and a selected therapy element. In particular, the connecting element provides physical contact between the first plate contact point associated with the selected conduit and the second plate contact point associated with the selected therapy element. A spring mechanism may also be provided within the interface system to ensure adequate electrical connection provided by the connecting elements. Further, the top cover 605 and the bottom cover 640 may together form a housing that may provide the interface system with a fluid-tight seal. As can be appreciated, the top cover may include an opening that is sealed with a flexible membrane so as to provide access to the first plate.

Figure 7:
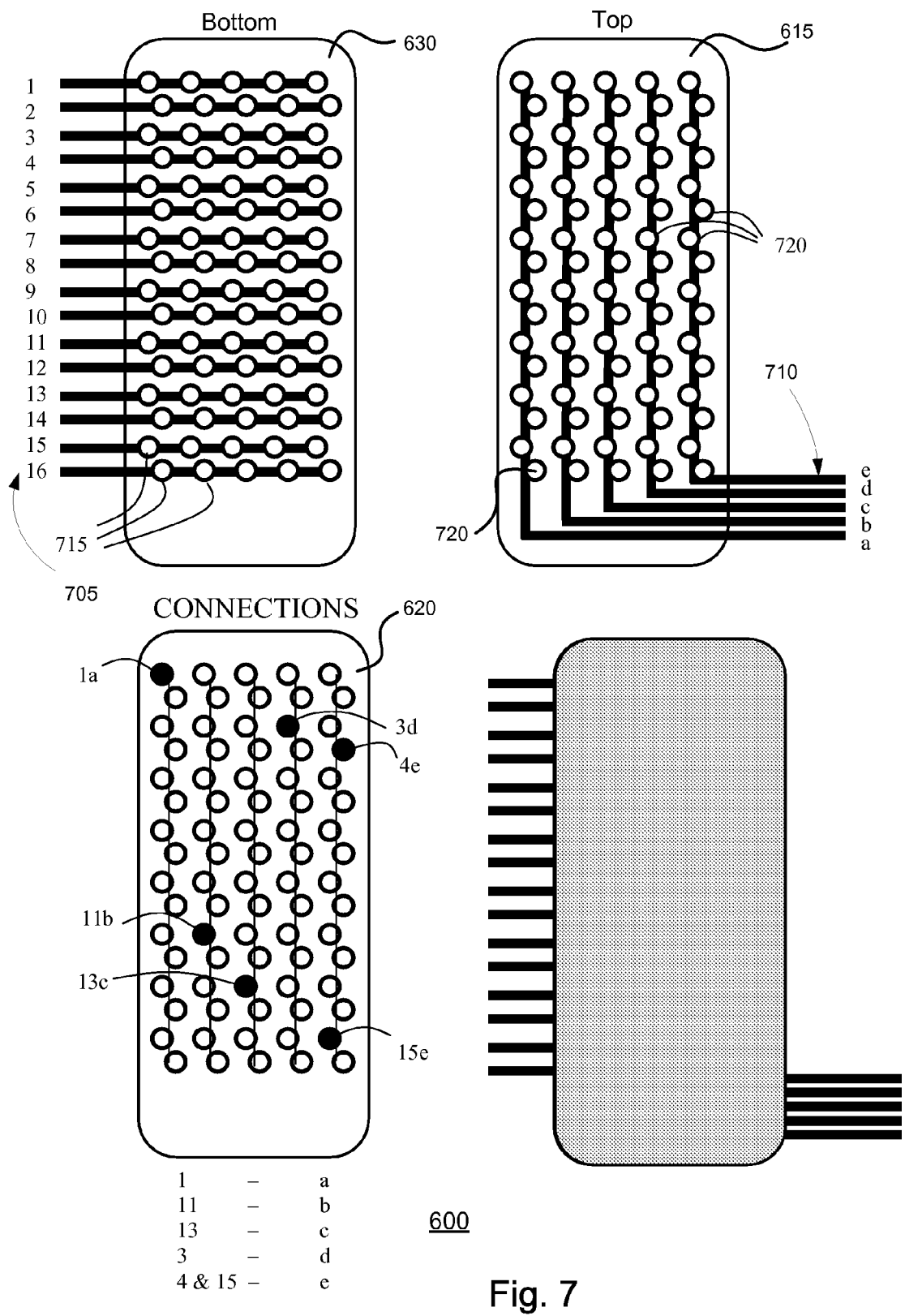
FIG. 7 is a schematic diagram illustrating one of many possible ways of connecting elements to selectively interconnect certain inputs to certain outputs within an implantable interface system in accordance with one or more aspects of the present invention.

To illustrate the operation of the interface system 600, FIG. 7 depicts an embodiment with specific components of the device, namely the top plate 615, the middle plate 620 (optional), and the bottom plate 630. The bottom plate 630 provides a geometry that enables connection of up to 16 therapy elements 705 (see also elements 130 and 140 of FIG. 1) to five conduits 710 (see also, conduits 150 of FIG. 1). As can be appreciated, however, some other number of therapy elements 705 and/or conduits 710 may be provided. Each therapy element 705 may be attached to the bottom plate 630 in a manner that provides connectivity to a plurality of base contact points 715. As depicted, the bottom plate provides connection for each therapy element 705 to five base contact points 715, each of which functions to provide selectable connection to a corresponding conduit 710. Similarly, the top plate 615 provides a geometry that enables each of the conduits 710 to be connected to a plurality of top contact points 720. As depicted, the top plate provides connection for each conduit 710 to sixteen top contact points 720, each of which functions to provide selectable connection to a corresponding therapy element 705. The base contact points 715 and top contact points 720 geometrically coincide. The interface system enables selective connections between certain base contact points 715 and top contact points 720 in order to produce a desired combination of connections between certain therapy elements 705 and conduits 710. For illustration, as depicted, connections 1a, 11b, 13c, 3d, 4e, and 15e are made by the interface system, with all other potential connections between base contact points and top contact points not enabled. This configuration connects therapy element 1 to conduit a, therapy element 11 to conduit b, therapy element 13 to conduit c, therapy element 3 to conduit d, and therapy elements 4 and 15 are both simultaneously connected to conduit e.

One skilled in the art will appreciate that there are many known ways to communicatively connect a desired subset of base contact points 715 to top contact points 720, and the means for connection may vary depending upon the application and may include, but are not limited to, galvanic connections such as may be provided by a connecting wire or solid state relay, optical connections, or fluidic connections such as may be provided by one or more valves. The interface system may enable easy selection of the desired connections, and ensure that the connections are robust. Techniques for selecting desired connections may include, for example, any of the following:

(a) mechanical means, such as by pressing one or more buttons that operate to toggle (or otherwise modify) the state(s) of particular connection(s);

(b) use of telemetry from a programmer device (e.g., using infrared, radio-frequency, or ultrasound) to toggle connections; or (c) use of an optional middle connecting plate 620, which may be inserted between bottom plate 630 and top plate 615, wherein the connecting plate 620 essentially serves as a mechanism to position one or more connecting pins through apertures geometrically aligned with top and bottom contact points, in order to provide connections between desired contact points when the plates 615, 620, and 630 are assembled together.

Thus, FIGS. 6-7 disclose details of embodiments of an interface system that allows a health care provider to adjust which conduits are connected to which therapy elements. It should be noted that the connecting pins 625, while depicted as elongated, may be any other shape such as spherical. Thus, numerous variations are possible and will be appreciated in light of the present disclosure.

Figure 8:
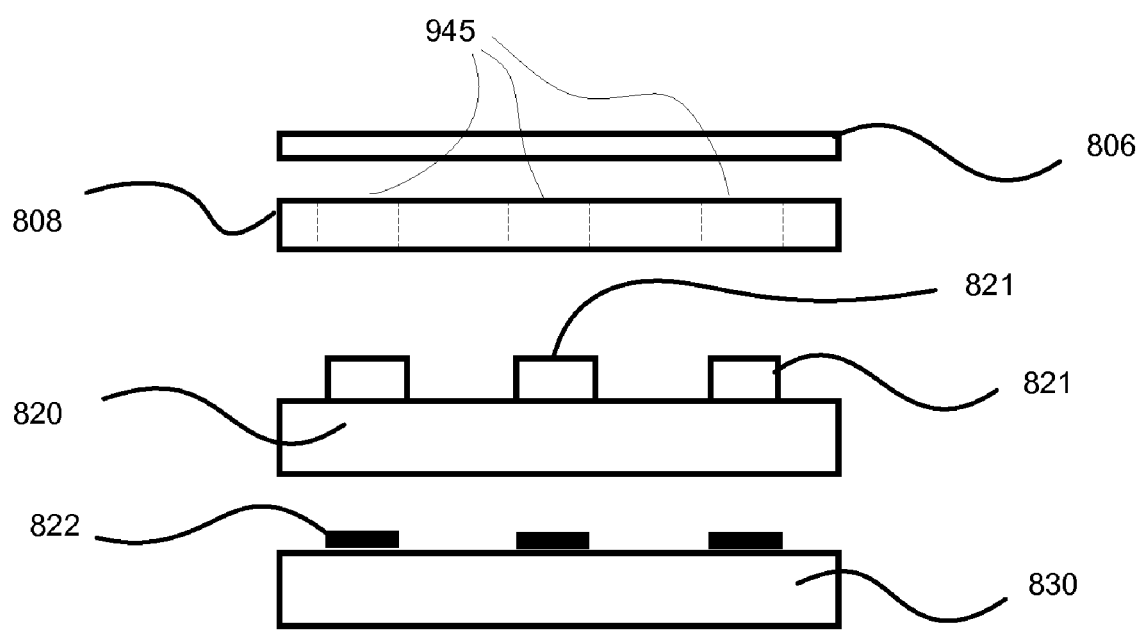
FIG. 8 is a simplified cross sectional view of an implantable interface system in accordance with one or more aspects of the present invention.

Turning to FIG. 8, a simplified exploded cross-sectional view of an embodiment of an alternate interface system is depicted. As depicted, a self-sealing membrane 806 or alternatively a sliding plate is positioned next to an access template 808, which is depicted as being biased. As will be discussed, the biased access template 808 may include a number of apertures 945. A top plate 820 is positioned below the biased access template 808 and includes a plurality of controller extensions 821. A bottom plate 830 is positioned below the top plate 820 and may include a number of contact points 822. It should be noted that, as discussed above, the elements depicted in FIG. 8 typically are mounted in a housing that is configured to support the various components in their appropriate positions relative to each other. It should be noted that the depicted arrangement is merely exemplary. For example, the membrane 806, which may be silicone or some other suitable material, may be mounted directly to the housing. As can be appreciated, the membrane 806 can act to prevent the influx of tissue and fluids that might otherwise block the apertures in the biased access template 808 (discussed below).

Figure 9A:
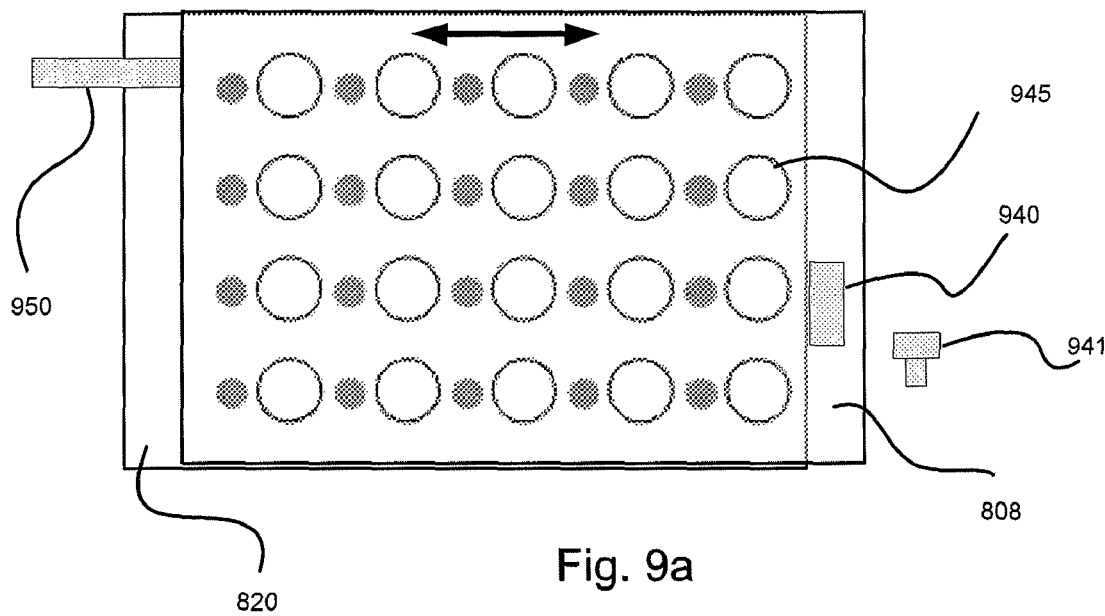
FIGS. 9a-9b illustrate an embodiment of an access template system in accordance with one or more aspects of the present invention.
Figure 9B:
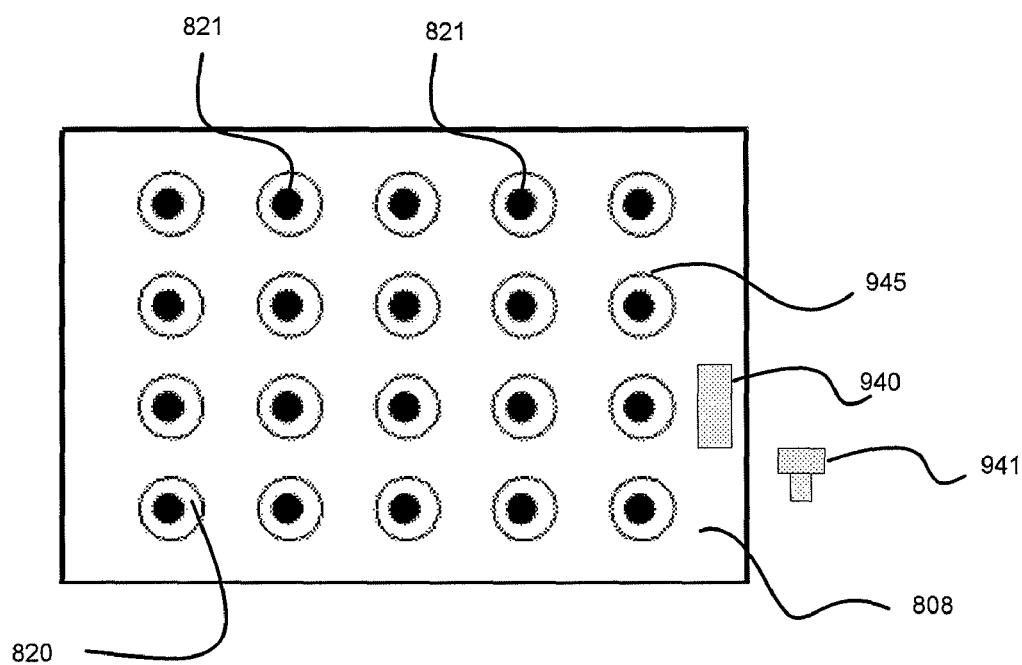

FIGS. 9a and 9b illustrate the biased access template 808 positioned above the top plate 820. As depicted, the biased access template 808 includes a plurality of apertures 945 and when the biased access template 808 is aligned with the top plate 820, the apertures 945 coincide with the controller extensions 821. When the biased access template 808 is in a first position as shown in FIG. 9a, however, the apertures 945 do not align with the controller extensions 821. Thus, to align the apertures 945 with the controller extensions 821, the biased access template 808 may be moved from a first position as depicted in FIG. 9a to a second position as depicted in FIG. 9b. However, a locking feature 940 may first need to be actuated or otherwise positioned in a non-locking position.

Figure 10A:
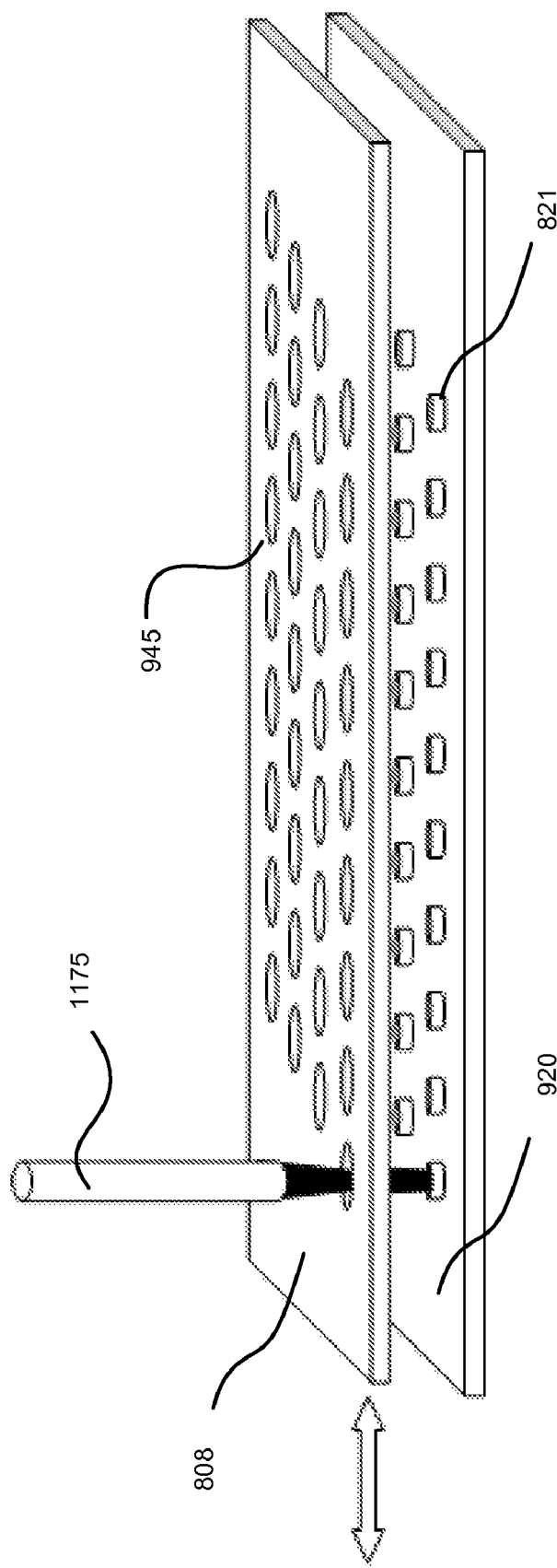
FIGS. 10a-c illustrate embodiments of access templates in accordance with one or more aspects of the present invention.
Figure 10B:
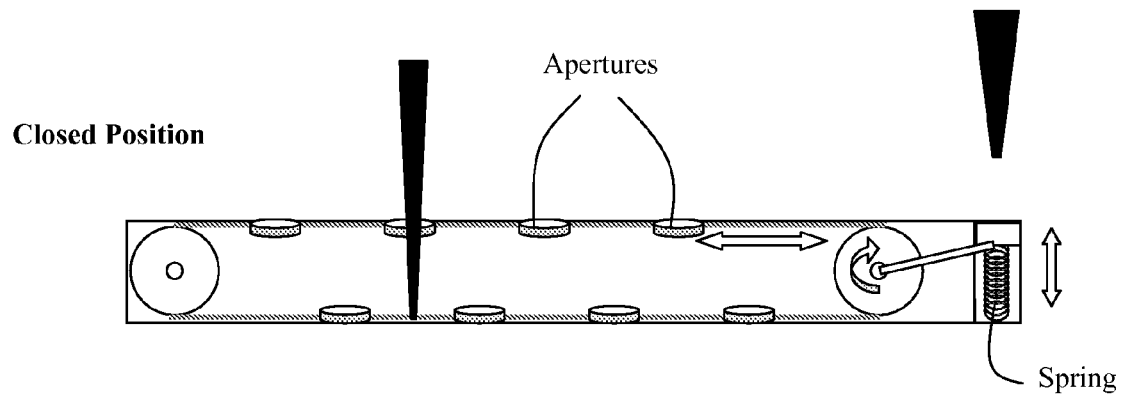
Figure 10C:
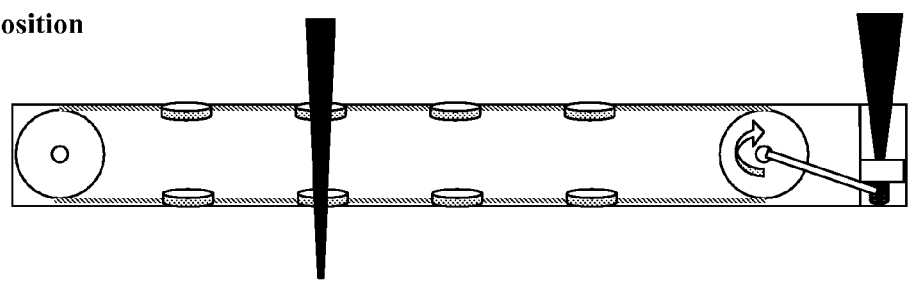

Turning to FIG. 10a, once the access cover 808 is positioned in the second or aligned position, a tool 1175 may be inserted through one of the apertures 945 so as to make contact with one of the controller extensions 821. By pressing on the controller extensions 821, the configuration of the interface system may be adjusted. The upper-most part of each controller extension 821 may be designed to allow stable coupling with the tool 1175 to avoid slippage. Referring to FIGS. 10b and 10c, another arrangement is depicted wherein tracks with a rack and pinion arrangement may be utilized to slide a plate with apertures over another to align the holes. It will be appreciated that any number of arrangements may be utilized to bias and move the access plate. For example, a spring mechanism may be utilized to align the plate between open and closed positions.

Figure 11:
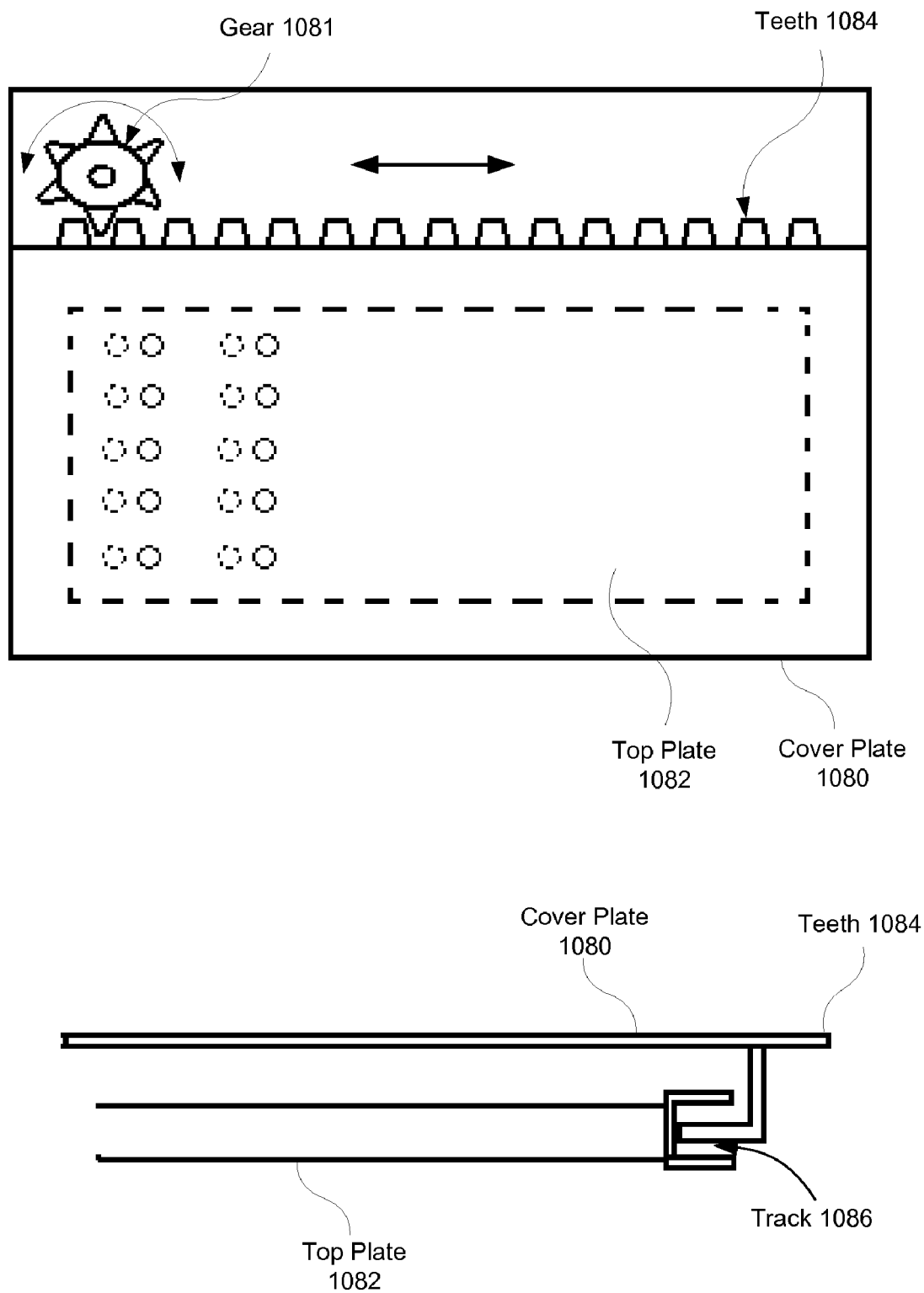
FIG. 11 illustrates yet another embodiment of an access template in accordance with one or more aspects of the present invention

FIG. 11 depicts an embodiment of a system for protecting the interface system. A gear mechanism 1081 may be utilized to engage with teeth 1084. Rotation of the gear 1081 causes the cover plate 1080 to move relative to the top plate 1082. A track 1086 helps to maintain the mating components. As one skilled in the art may appreciate, the top plate and the bottom plate of the interface system may utilize tracks to stabilize and govern the movement of the cover plate. Optionally, as depicted, the cover plate may have a lip that engages with a track that may be, for example, on the top plate.

Figure 12:
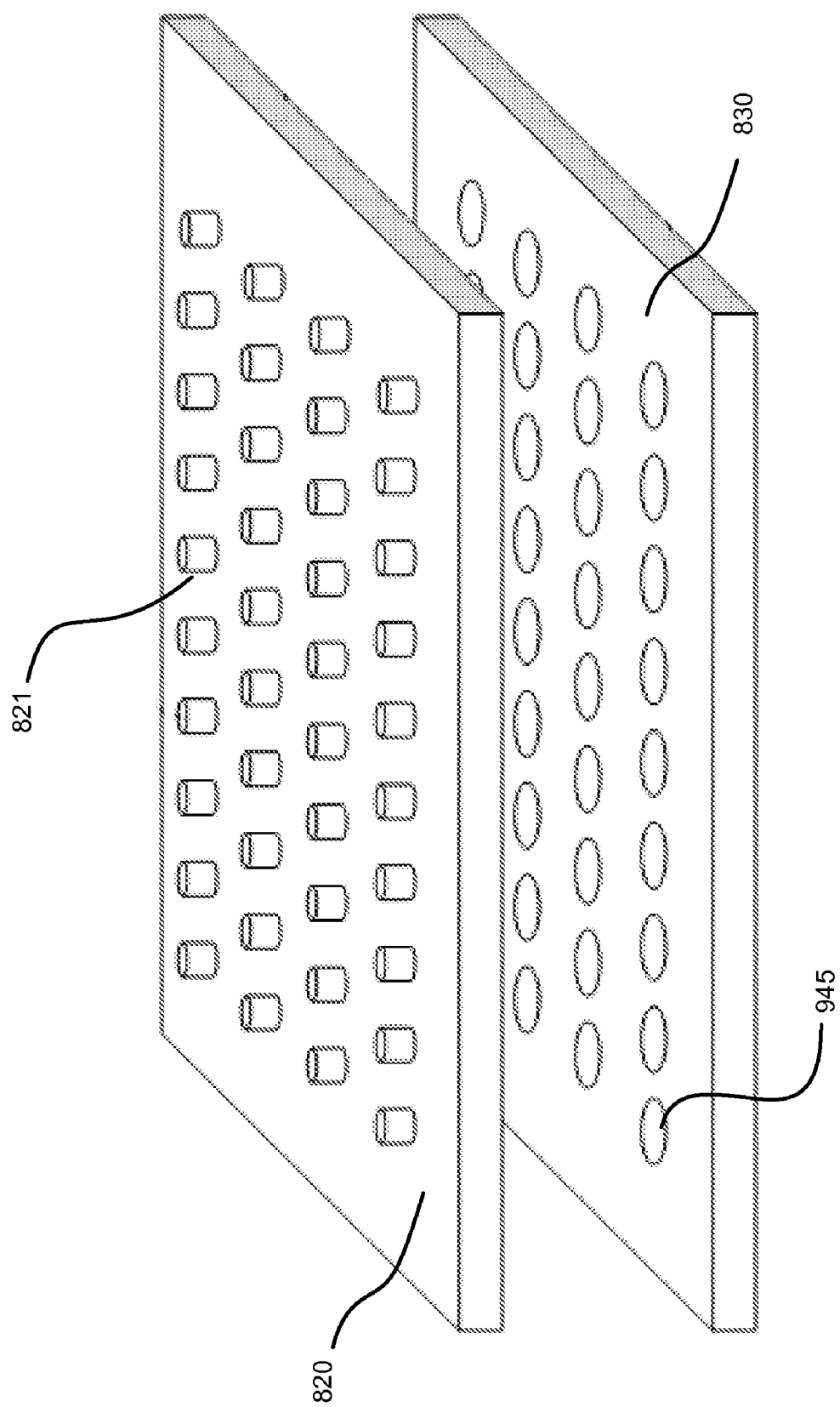
FIG. 12 illustrates an embodiment of a top and bottom plate in accordance with one or more aspects of the present invention.

Referring to FIG. 12, a top plate 820 is depicted as positioned above the bottom plate 830. As can be appreciated, each of the controller extensions preferably will be aligned with a contact pad 945 positioned on the bottom plate 830. By activating the controller extension 821, an electrical connection may be made.

Referring back to FIGS. 9a and 9b, it should be noted that the biased access template 808 is depicted as being biased toward the first position (depicted in FIG. 9a) by biasing element 950. Various methods of biasing may be used, such as, but without limitation, a spring element, a compressible cylinder or the like. As the use of a biasing element is known, no further discussion will be provided.

In an alternative embodiment, an access template may be provided that is not biased. Regardless of the existence of the biasing element, the access template may be locked in a first position with a locking feature 940 and to move the access template to the second position may require the pressing of one or more buttons so as to allow unlocking of the access template and allow it to translate to the second position. As can be appreciated, the use of more than one optional locking feature 940 provides additional security that incidental contact will not allow the access template to translate into an aligned position. Further security may be provided by requiring the insertion of one or more keys 941 so as to unlock the one or more locking features 940. In addition, multiple access templates may be provided and two different access templates may be configured so that the access templates are each translated in different directions in order to align the apertures with the controller extensions. Thus, looking at FIG. 9a, a second access template 808 (not shown for purposes of clarity) could be provided that translated in a different direction than the access template 808 that is depicted. Each of the access templates may include a separate and distinct locking feature or a single locking feature may be used for multiple access templates.

Figure 13:
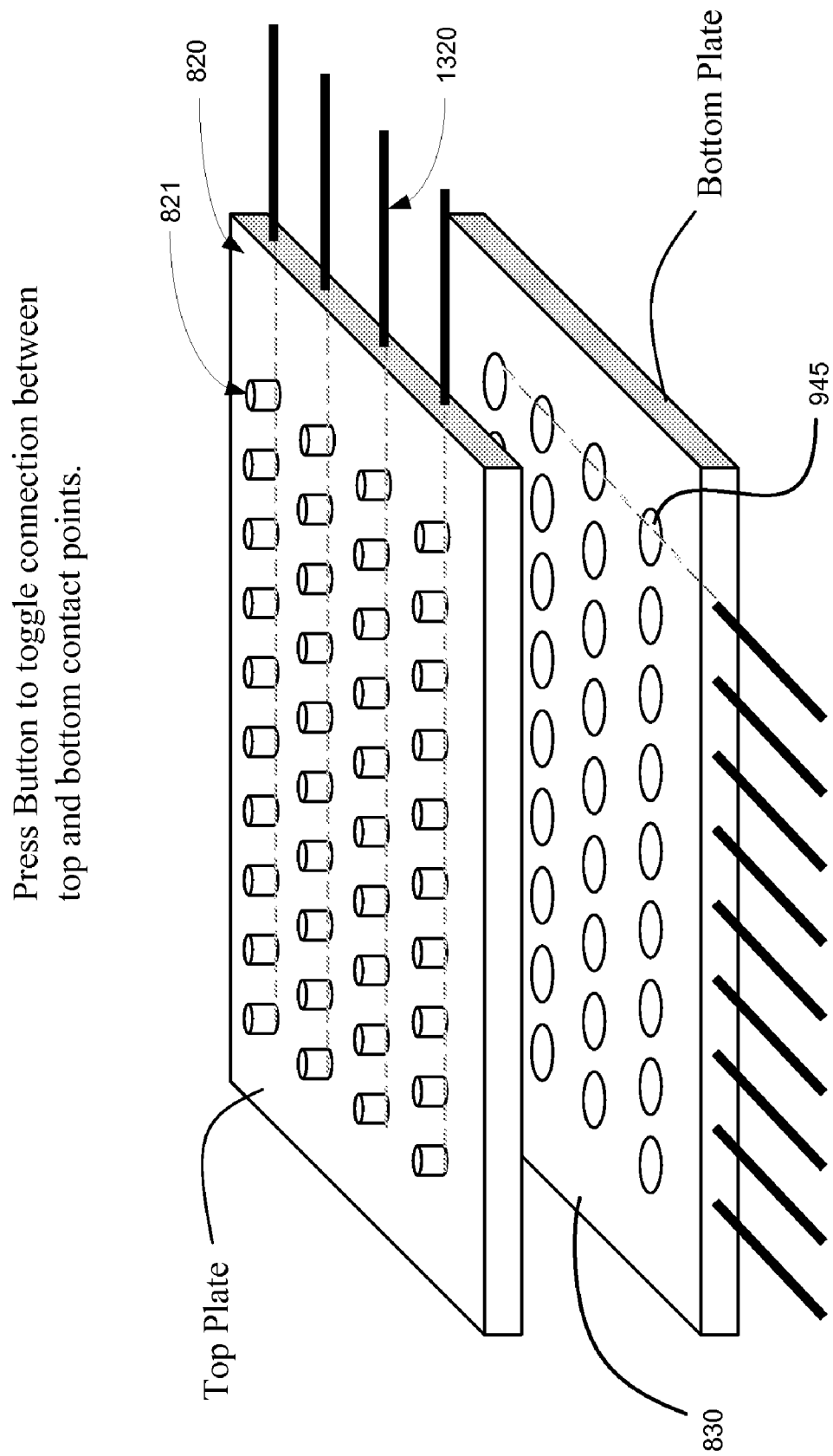
FIG. 13 illustrates a top and bottom plate having a conduit lead to link to the multiple controller extensions in accordance with one or more aspects of the present invention.

It should be noted that, similar to the embodiment depicted in FIG. 7, multiple controller extensions 821 may be connected to a single conduit. In an embodiment as depicted in FIG. 13, a conduit 1320 may link to the multiple controller extensions 821. Depending on the position of the linked controller extensions, this allows the conduit 1320 to electrically connect to multiple contact pads 945, each of which may be connected to a separate therapy element. As can be appreciated, displacing the controller extension 821 allows an electrical connection between contact pads 945 with conduit 1320.

Figure 15:
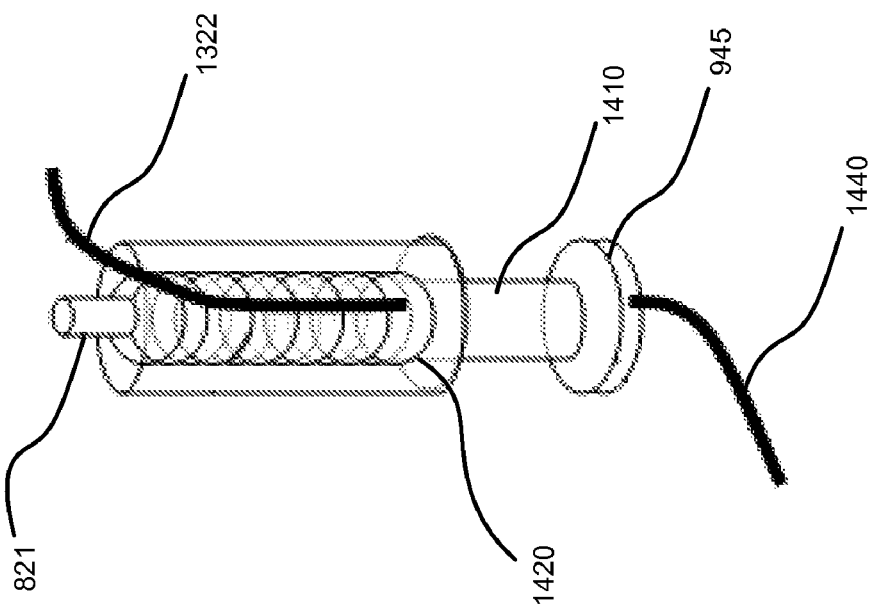
FIGS. 14-15 illustrate an embodiment of a connecting element/mechanism in accordance with one or more aspects of the present invention.
Figure 14:
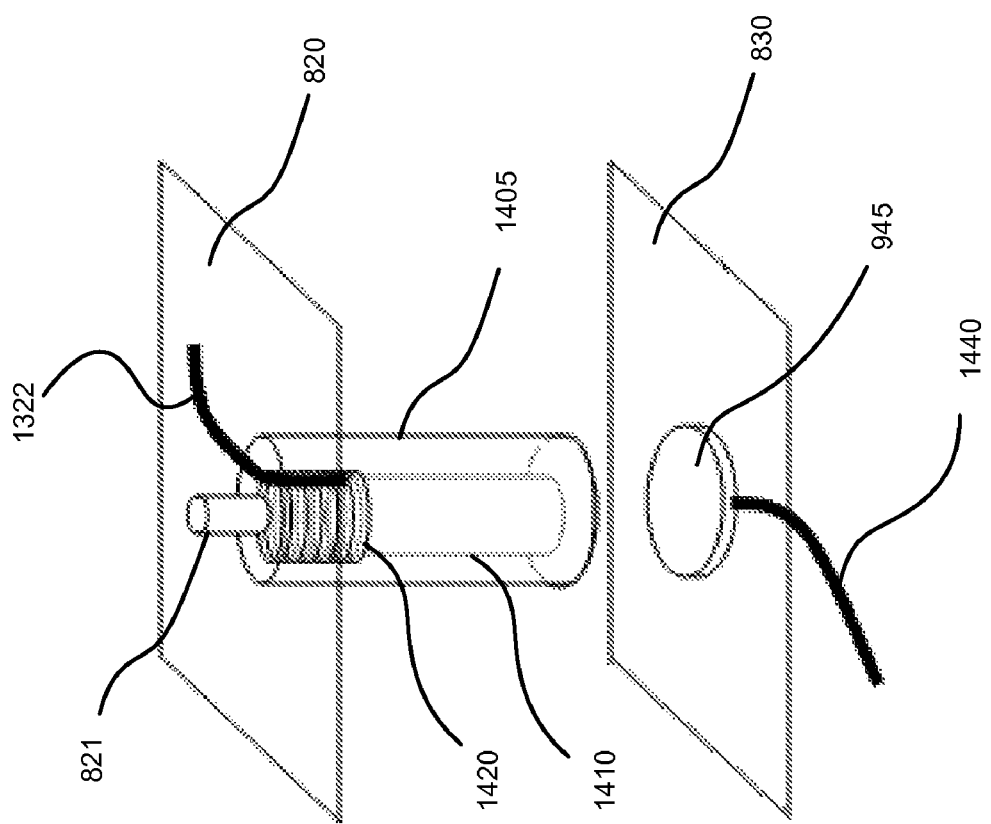

FIGS. 14 and 15 illustrate an embodiment of how depressing the controller extension 821 can create the electrical connection. Looking first at FIG. 14, a connector housing 1405 is mounted to the top plate 820 and the controller extension extends above the top plate 820. A connector pin 1410 is positioned in the connector housing 1405 and is biased in an open position by the biasing element 1420. As depicted, a conduit 1322 is connected to the biasing element 1420. Positioned below the connector housing 1405 is a contact pad 945 that is supported by the bottom plate 830 and is connected to a therapy element 1440.

FIG. 15 removes the top and bottom plates 820 and 830 for ease of illustration. Pressing down on the controller extension 821 causes the connector pin 1410 to translate until in comes into contact with the contact pad 945. The connector pin 1410 may be held in position by a detent that prevents the connector pin 1410 from translating back to the open position until the controller extension 1410 is pressed again (in a manner similar to operation of a retractable pen). Alternatively, the connector pin may be rotatably supported by a thread and contact between the connector pin 1410 and the contact pad 945 may be accomplished by rotating the connector pin 1410 in a manner similar to how a screw is used.

Figure 16:
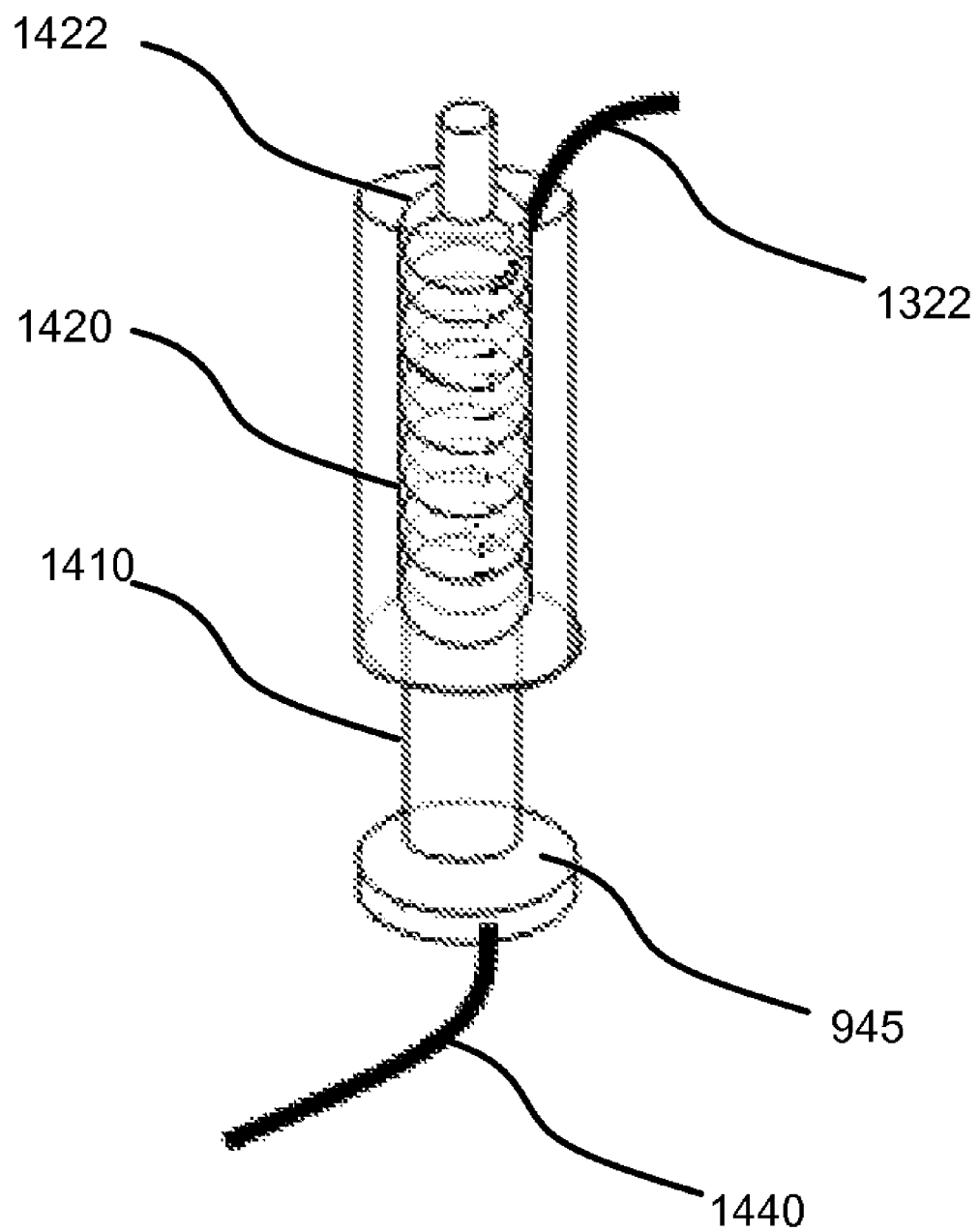
FIG. 16 illustrates an alternative embodiment of a connecting element in accordance with one or more aspects of the present invention.

It should be noted that if a translating connector pin 1410 is used that is similar to what is disclosed in FIGS. 14-15, it may be beneficial to reduce the distance the conduit 1322 translates when the connector pin translates to the open position. Therefore, FIG. 16 illustrates an embodiment wherein the conduit branch 1322 is connected to an upper portion 1422 of the biasing element 1420. As can be appreciated, minimizing the amount of translation of the conduit 1322 can be useful in increasing the robustness of the design and in avoiding unnecessary wear.

As can be appreciated, the ability to control which conduits are coupled to which therapy elements helps minimize the need for surgical replacement or repositioning of therapy elements in the event that they break down, migrate or the patient's monitoring or therapy target(s) or condition changes after the therapy elements are implanted. Instead, the conduits may be coupled to alternative therapy elements.

Thus, in the above two embodiments, connectors from one plate make contact with another plate only when deployed. The deployment of the connectors may be achieved through a variety of techniques including, but not limited to, spring mechanisms (that operate in a manner similar to that of retractable ball-point pens), magnets, radio-frequency tags, ultrasound, and/or infrared light. Where a spring mechanism is utilized, the spring mechanism may be depressed with a "pointer" (e.g., tool 1175 of FIG. 11) (the top plate has openings over each spring mechanism) that is inserted through the scalp using a needle-like tool. The upper most part of the upper portion 1422 of the biasing element 1420 may be designed to allow stable coupling with the tip of "pointer" to avoid slippage. The person changing the connections will have a "template" plate which is identical to the top one mounted in the skull and which will be placed over the scalp and aligned with the one underneath it. Fiducials made of plastic, noble metals or ink ("tattooed") detectable on the scalp (visible, palpable or amenable to imaging) defining the boundaries of the skull mounted interface, will allow precise superposition of the template over the top skull mounted plate. The same scheme may be used with a pencil magnet except that in this case the scalp will not be pierced.

It should be noted that in addition to electrical connectors, other types of connectors such as optical connectors can be similarly configured. As can be appreciated, a first light pipe with a plurality of passageways could be aligned with a plurality of light pipes and by selectively connecting the first light pipe to one of the plurality of light pipes, optical signals could be routed as desired.

In an embodiment, the housing of the interface system may include 5 holes in the four corners and center of the outer surface of the skull-mounted connector, where each hole has a pin which is removable and protrudes from the closed scalp.

An indelible biocompatible ink (such as a tattoo) or some other fiducial may be used to mark the scalp around the protruding pins and after this has been done, the pins may be removed. These scalp fiducials may be subsequently used to guide alignment with the access template, which will be positioned within the interface system. It should be noted that some other number of fiducials may be used, however, at least three fiducials is preferred so as to ensure a proper orientation.

As noted above, while electrical signals can be recorded and electrical stimulation may be used to treat a patient, pharmaceutical compounds and medicaments may be beneficial in treating a patient. In addition, the ability to collect fluids from various portions of the patient's brain may be helpful in detecting and analyzing the patient's condition.

Figure 17:
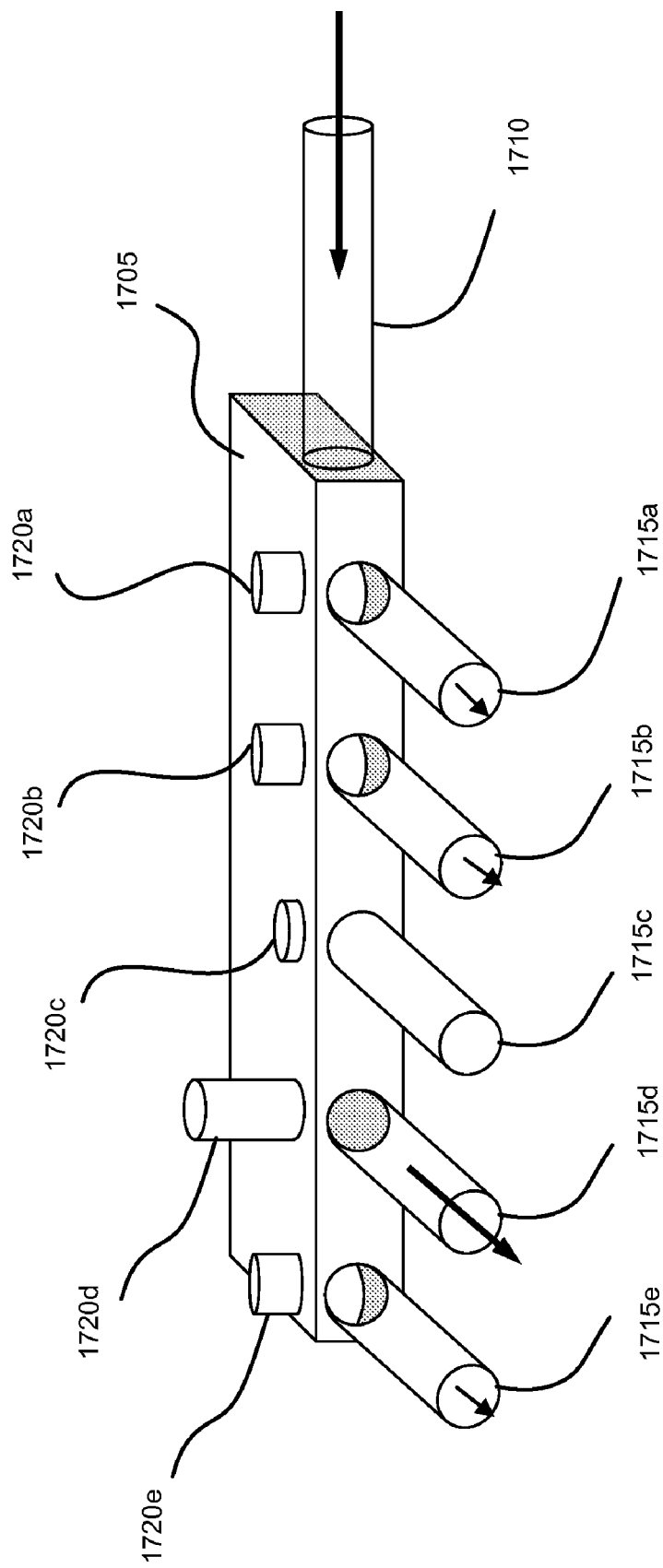
FIG. 17 illustrates an embodiment of a flow module in accordance with one or more aspects of the present invention.

FIG. 17 illustrates an embodiment of an interface that may be used to adjustably deliver or collect substances to and from the patient's tissue such as a brain. Flow module 1705 may be positioned in a manner similar to corresponding structure depicted in FIG. 8 (except bias plate and protective member are not depicted in FIG. 17). However, as can be appreciated, the bottom plate is not required to direct the flow of substances. As depicted, a fluid enters the module 1705 through conduit (or inlet tube) 1710. Depending on the configuration of the valves 1720a-1720e, fluid is directed out the therapy elements (or delivery tubes) 1715a-1715e. It should be noted that while the flow of fluid is depicted as proceeding from the inlet tube 1710 toward the delivery tubes 1715, a reverse direction of flow is also contemplated. Furthermore, while FIG. 17 depicts a single source supplying a plurality of delivery tubes, in an alternative embodiment the delivery tubes could be distinct sources of fluids that supply the inlet tube 1710. As can be appreciated, this could be used to collect samples of fluid from the patient and could also be used to adjust the delivery of a compound fluid to a single port or catheter. The valves in FIG. 17 are depicted in three configurations, closed (as shown by valve 1720c), partially open (as shown by valves 1720a, 1720b and 1720e) and fully open (as shown by valve 1720d).

Figure 18A:
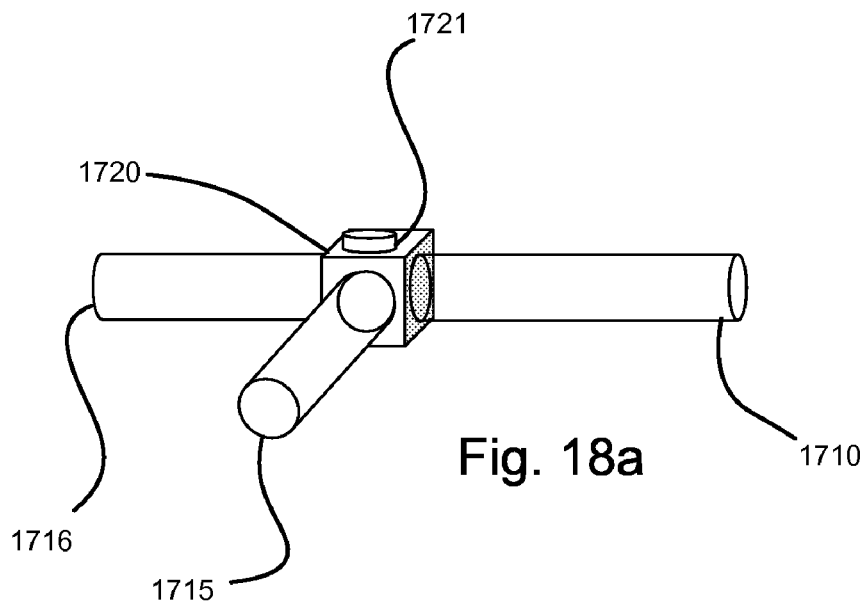
FIGS. 18a-18c illustrate an embodiment of a valve in different configurations in accordance with one or more aspects of the present invention.
Figure 18B:
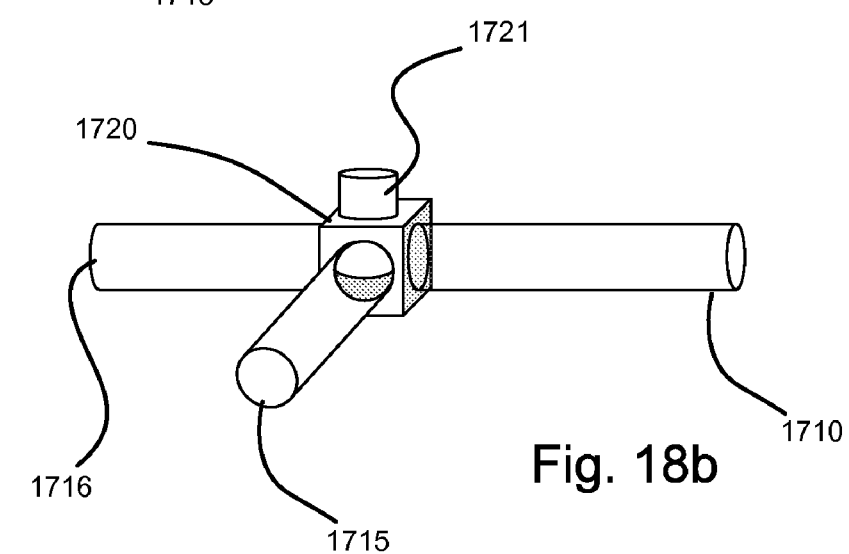
Figure 18C:
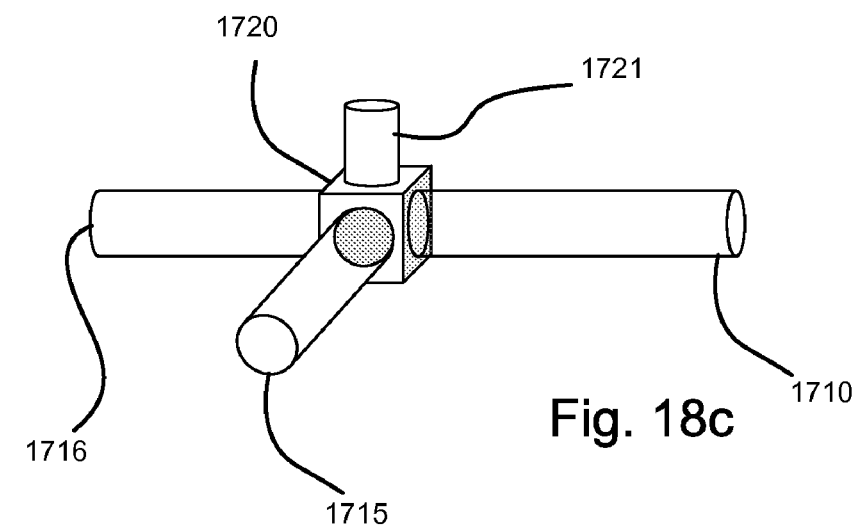

FIGS. 18a-18c illustrate similar configurations without the module 1705. It should be noted that while the valve 1720 is depicted as being closed when button 1721 is depressed, the reverse is also contemplated.

FIGS. 19a-19d illustrate embodiments of valves 1720 that include an outer wall 1910, a core 1920 that includes a fluid passageway 1925 and multiple tubes 1710, 1715, 1716. As can be appreciated, FIGS. 19a-19d illustrate the core 1920 being rotated around in different positions so that the fluid passageway 1925 couples different tubes together. As depicted in FIG. 19d, the flow from inlet tube 1710 is evenly distributed to delivery tubes 1715, 1716. In an embodiment, the depressing of the button 1721 (FIGS. 18a-c) may cause the core 1920 to rotate (through known techniques such as "helical" or other guided threading to produce rotation) so that different tubes are coupled together (or so that no tubes are coupled together). In an alternative embodiment, the core 1925 may be configured in the desired position when installed. In another alternative embodiment, translation of the button 1721, which may include rotation, may allow for the rotational orientation of the core to be adjusted. Preferably the orientation of the core will be apparent and to aid in this matter, an asymmetric key (not shown) may be required to translate the button.

Figure 20:
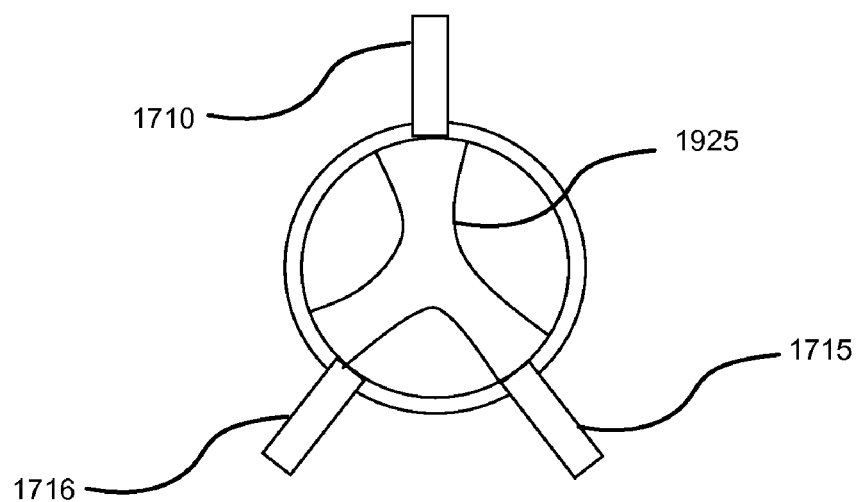
FIG. 20 illustrates a cross-section of embodiment of a valve configured to provide variable flow in accordance with one or more aspects of the present invention.

While FIGS. 19a-19d illustrate a full coupling between the fluid passageway 1925 and the tubes, in an alternative embodiment as depicted in FIG. 20, the fluid passageway 1925 may provide for a reduce flow rate to one of the tubes versus the other tubes. In an embodiment, the flow from tube 1710 may be distributed to delivery tube 1715 in a ratio of 9:1 versus delivery tube 1716. As can be appreciated, if the delivery tube 1715 supplies other delivery tubes than such a flow distribution may be useful to ensure relatively consistent flow is provided to each delivery tube. The varying flow rate may be achieved with fluid passageways 1925 having differing diameters and/or offsetting of the fluid passageways 1925 from corresponding tubes 1710, 1715, and 1716.

Figure 21:
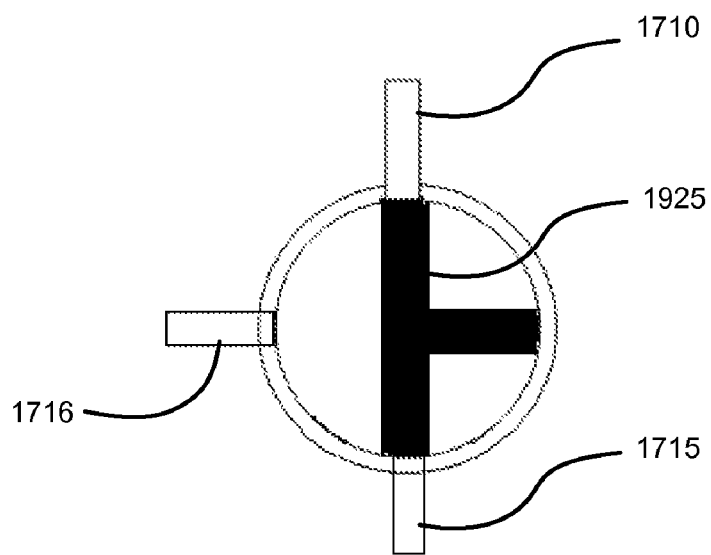
FIG. 21 illustrates a cross-section of an embodiment of a valve configured to be installed in series in accordance with one or more aspects of the present invention.

It should be noted that FIG. 17 illustrates a number of valves in series. In an embodiment it may be desirable to always direct flow through each valve but to control whether the flow is directed out the associated delivery tube. To provide such control, in an embodiment the flow passageway 1925 may be configured as depicted in FIG. 21. In the depicted position the flow would pass from inlet tube 1710 to delivery tube 1715 but would not be directed toward delivery tube 1716. By rotating the orientation of the flow passageway 1925 180 degrees, however, fluid may be directed toward the delivery tube 1716.

It should be noted that multiple flow passageways may be provided in the core 1920, with each flow passageway stacked on top of another flow passageway. In such a configuration, depressing the button 1721 will align a different flow passageway with associated tubes. This depression can toggle the state of an associated valve, for example, by causing a rotation to allow flow passage in any number of combinations.

Figure 22:
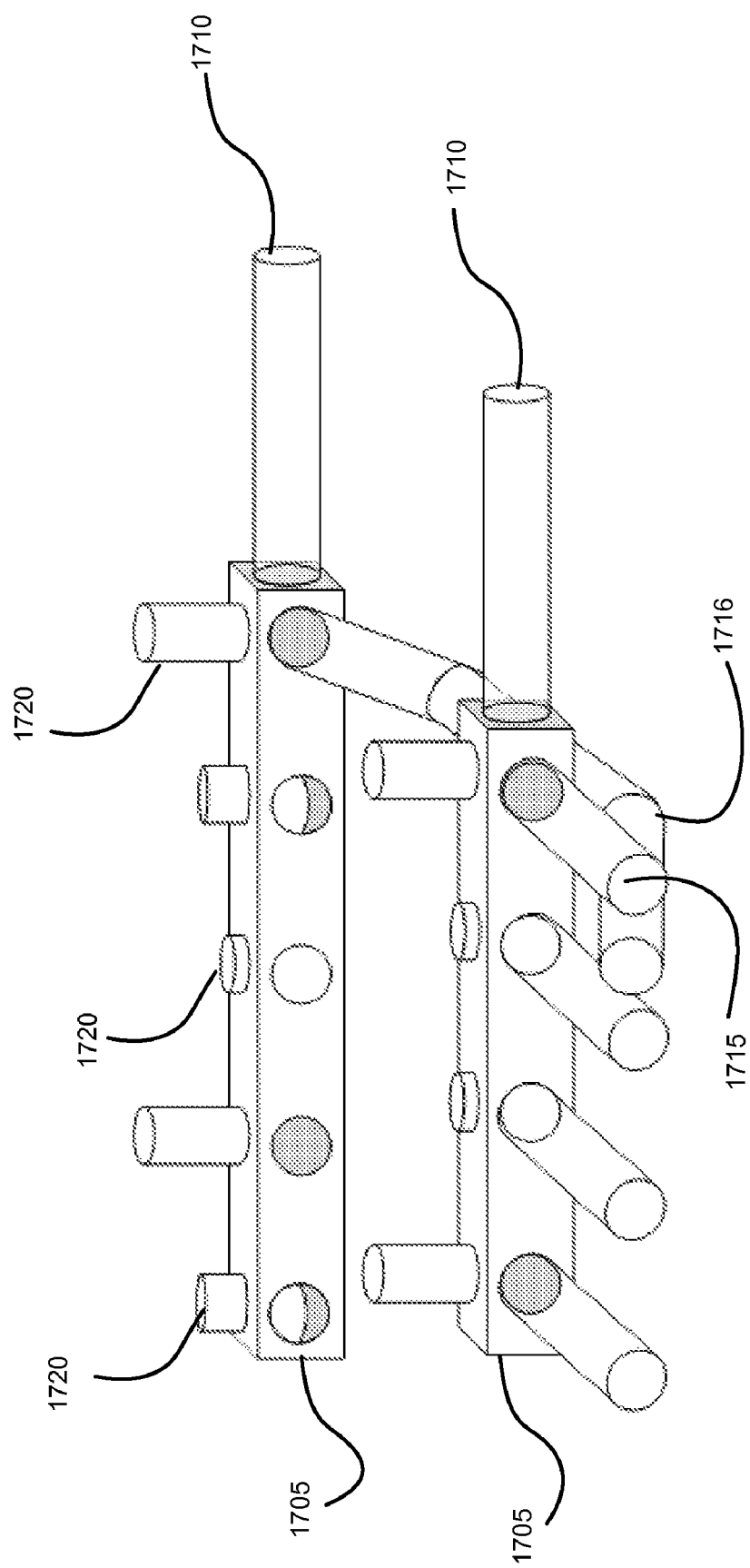
FIG. 22 illustrates an embodiment of two flow modules configured to be used together in accordance with one or more aspect of the present invention.

As depicted in FIG. 22, multiple flow modules 1705 may be used together. As can be appreciated, this allows delivery of multiple substances to similar locations.

Figure 23:
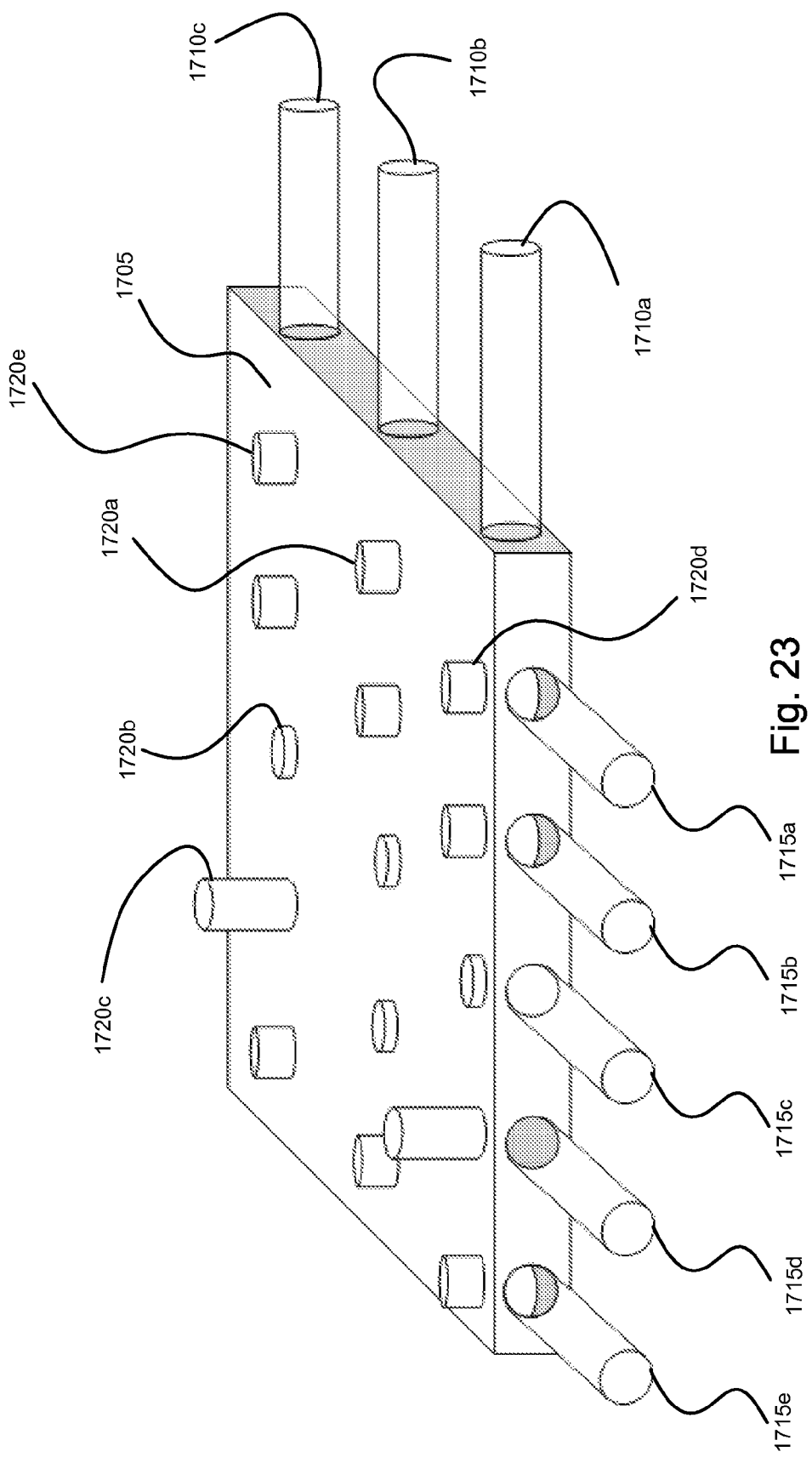
FIG. 23 illustrates an embodiment of a flow module with multiple inputs in accordance with one or more aspects of the present invention.

FIG. 23 illustrates an alternative embodiment of a complex flow module 1705. In an embodiment, each of the conduits (or inlet tubes) 1710a-1710c can be configured to direct fluid to each of the therapy elements (or delivery tubes) 1715a-1715e, depending on the configuration of the valves 1720. In an embodiment, each of the outlet/delivery tubes 1715 is fed by the three inlet tubes 1710a-1710c. Thus, as depicted, the fluid exiting delivery tube 1715a includes fluid received from valves 1720a, 1720d and 1720e. Flow may pass through each valve 1720 even if each valve 1720 is not used to direct flow toward a delivery tube 1715. Thus, for example, flow from inlet tube 1710c provides flow to open valve 1720c even though valve 1720b is closed.

FIG. 24 illustrates a simplified embodiment of a fluid delivery system. Plate 2410 may be moved utilizing a mechanism such as, for example, a rack and pinion or microstepper motors. The pump 2405 includes a first reservoir 2406 and a second reservoir 2407, each with a different medicament stored within the reservoir. By sliding the plate 2410 clockwise, ports 2415 can be aligned with pump tubes 2420. As can be appreciated, this allows for a graduated response. In a first position no fluid is provided. In a second position, a single pump tube 2420 is supplying fluid from a first reservoir 2406. In a third position, two pump tubes are supplying fluids from a first reservoir and one pump tube is supply fluids from a second reservoir 2404. Thus, such a system provides a tiered response. Those skilled in the art would appreciate that plate 2410 may be moved clockwise or counterclockwise. Also, the number and diameter of ports 2415 and the distances from their center to the outer edge of each set of tubes 2420, and the ratio of diameter of 2415 to diameters 2420 may be modified to so that a large number of adjustments may be effected according to the application.

Figure 25C:
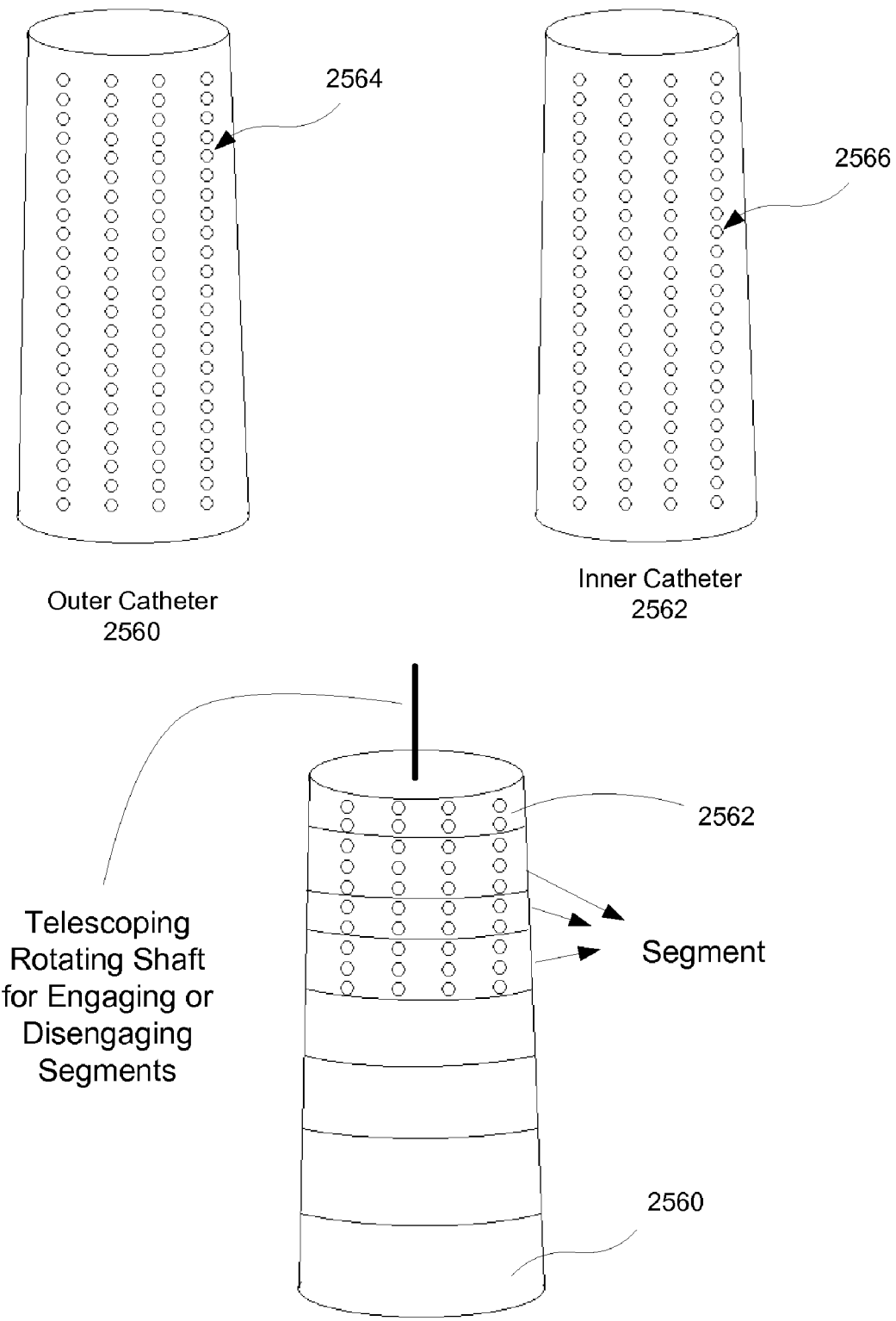

FIGS. 25a and 25b illustrate another aspect that may be used in accordance with the present invention. These embodiments may be therapy elements where selectivity of fluid delivery is achieved along the body of the therapy elements. A tube 2510 is provided with a plurality of ports 2515 that are closed (i.e., not exposed to fluid) and a number of ports 2516 that are open (i.e., exposed to fluid). A slidable plate 2520 is positioned within the tube 2510 and the position of the slidable plate 2520 may be adjusted with member 2530. Member 2530 may, for example, be associated with a controller extension (discussed above). By translating the slidable plate 2520, more or less of the ports may be blocked or unblocked. Thus, such a system may provide for more fine tuned control over delivery of fluids. As can be appreciated, the slidable plate 2520 can be configured so that it blocks a first set of ports in a first position, blocks a second set of ports in a second position and blocks a third set of ports in a third position.

Although ports are shown in a single line for simplicity, it will be appreciated that the ports 2515 and 2516 may be in any direction along the tube 2510. For example, there may be an array of ports 2515 and 2516 along the entire surface of tube 2510. Moreover, plate 2520 may alternatively be a hollow cylinder to which drugs arrive via a conduit and then plate 2520 delivers fluid only to the adjoining port that it engages. Even further, there may be multiple plates 2520 in tube 2510 to provide additional flexibility. Alternative embodiments are also possible, for example, the embodiment of FIG. 25c having an outer catheter 2560 having a plurality of ports 2564 and a rotatable inner catheter 2562 having a plurality of ports 2566. Once inserted within the outer catheter 2560, the inner catheter 2562 may engage or disengage ports.

In an embodiment, the length of the slidable plate 2520 may be increased so that the slidable plate 2520 extends a substantial length down the tube 2510. In such an embodiment, the slidable plate 2520 may include a pattern of openings that matches a pattern of ports in the tube 2510 such that moving the slidable plate 2520 a small distance causes a substantial change in the number of ports that open or blocked by the slidable plate. As can be appreciated, the ports may be evenly or variable spaced and in a closed position, none of the openings of the slidable plate will be aligned with the ports in the tube 2510.

It will be appreciated that any number of configurations may be implemented in accordance with the invention. For example, as discussed, the interface system (and corresponding layout of the associated components) may take the form of any number of geometric shapes. Moreover, connecting pins 625 may take the form of any number of connecting elements for providing electrical connectivity. In an embodiment, the controller extensions may be translatable via the application of magnet force. As can be appreciated, such a configuration will allow the individual adjusting the delivery of stimulation to adjust which electrodes are connected to which conduits without the need to pierce (with a "needle") or make a small incision in the patient's tissue.

It should be noted that the control of the position of the valves and position of the connector extension 821 may be automated and controlled via a controller, which may be programmed via a wireless manner with a programmer such as a physician programmer. The advantage of using mechanical controlling is that no electrical power is required to change the configuration.

The interface system disclosed above provides the ability to selectively identify those therapy elements that should be operable by the medical device system. The therapy elements may be selected initially during implant but may also later be modified via use of the key and/or through a minimally invasive procedure. For example, in the embodiment of a circular interface system (FIG. 3), the key (keyhole not shown) may serve as a rotatable dial to facilitate the precise alignment (and subsequent adjustment) between the top plate and base plate.

Moreover, the ability of the interface system to connect more than one implanted element in tissue together into a single connection in the device (e.g., as depicted in FIG. 7 for therapy elements 4 and 15 connected to conduit e), enables the delivery of therapy to multiple sites using a single device output. In the aforementioned example, if the therapy modality is electrical stimulation, then the therapy elements (i.e., stimulation contacts) 4 and 15 may be "tied together" by the interface system and treated as a single cathode or anode for delivery of stimulation current. Similarly, when used for communication in the reverse direction (when the implanted elements can function as sensors) this feature enables the device to monitor an aggregate signal derived from a plurality of sensors in spatially economic and cost-effective ways, since the number of required device input ports and associated hardware (amplifiers, A/D converters, etc.) may be reduced. The "tying together" of multiple contacts may be applied, for example, to seizure detection and localization of the focus/foci from which they originate in the brain. By way of illustration, suppose for example, that a subject has 64 implanted contacts, with 32 of them located in the left hemisphere (8 contact electrode leads placed in each of the anterior, medial, and posterior temporal lobe, and an 8 contact lead placed in the frontal lobe) and 32 in the right hemisphere (homologously placed). Rather than require an equal number of device input ports and associated hardware (in this case, 64) to condition and analyze all available signals, the approach described herein reduces the amount of hardware required in the device, in embodiment, to only 8 device input ports, while retaining the ability to access any subset, or the entire set of the elements implanted within the tissue. In particular, suppose that the patient has an implanted seizure monitoring device which is limited to 8 inputs but there are 64 sensors. Since seizures may be detected in an aggregate signal, which functions as a weighted sum of voltage levels from the individual sensor locations, one may use a 64×8 interface system and connect each of the eight 8-contact electrode leads, each corresponding to a different brain region, to produce eight respective lead-aggregate interface system connections to the ports of the seizure monitoring device (using one port for each aggregated brain region signal covered by its respective lead). Once the patient has been monitored so as to capture a sufficient number of representative seizures, the process of more precise localization (identification of the sites/sensors most frequently involved in seizures) may begin. This may be accomplished via the interface system by disabling those leads that are not associated with the brain region(s) from which seizure begin. This process may be repeated until the lead or lead(s) corresponding to the seizure focus/foci are determined, after which the process can be refined to select relevant subsets of individual sensors from the remaining leads, which can be isolated and individually monitored until the optimal set of sensors is determined. This optimal subset of sensors, and the procedure used to identify them, can also provide improved efficacy of therapy via selective delivery to the precise site(s) from which seizures originate.

The usefulness of the invention should be apparent to one skilled in the art. The use of any and all examples or exemplary language herein (e.g., "such as") is intended merely to better illuminate the invention and does not pose a limitation on the scope of the invention unless otherwise claimed. No language in the specification should be construed as indicating any non-claimed element as essential to the practice of the invention.

The present invention has sometimes been described in terms of preferred and illustrative embodiments thereof. Numerous other embodiments, modifications and variations within the scope and spirit of the appended claims will occur to persons of ordinary skill in the art from a review of this disclosure.

We claim:

1. An implantable interface for a medical device system comprising:
   (A) a top plate;
   (B) a base plate;
   (C) a plurality of therapy elements, each therapy element being associated with at least one base contact point in the base plate;
   (D) a plurality of conduits, each conduit having a first end coupled to at least one top contact point in the top plate and a second end capable of being coupled to a monitoring or therapy device; and
   (E) a middle plate positioned between the top plate and the base plate, the middle plate including at least one aperture;
   (F) at least one removable connecting element selectively positionable between the top plate, middle plate, and the base plate to provide electrical connection between a first conduit and a first therapy element, the removable connecting element configured to provide physical contact between the top plate and base plate through the at least one aperture of the middle plate, wherein the at least one removable connecting element is configured to be repositioned to provide electrical connection between a second conduit and a second therapy element; and
   (G) a spring mechanism to facilitate electrical connection provided by the at least one removable connecting element.

2. The interface of claim 1, wherein the connecting element is a pin.

3. The interface of claim 2, wherein the shape of the connecting pin is a sphere.

4. The interface of claim 1, wherein the connecting elements provide electrical connection between the at least one top contact point associated with the first conduit and the at least one base contact point associated with the first therapy element.

5. The interface of claim 1, wherein each therapy element is a sensor.

6. The interface of claim 1, wherein each therapy element is associated with a lead implantable within a brain of a patient, the lead having a proximal end coupled to the base plate and a distal end having the associated therapy element to sense electrical signals or sense electrical signals.

7. The interface of claim 1, wherein each therapy element is associated with a lead implantable within a brain of a patient, the lead having a proximal end coupled to the base plate and a distal end having the associated therapy element to deliver electrical stimulation within the brain of the patient.

8. The interface of claim 1, further comprising a cover for the interface system providing a hermetic seal.

9. The interface of claim 1, further comprising a locking feature and a key.

* * * * *